US006270478B1

(12) United States Patent
Mernøe

(10) Patent No.: US 6,270,478 B1
(45) Date of Patent: Aug. 7, 2001

(54) INFUSION PUMP SYSTEM AND AN INFUSION PUMP UNIT

(76) Inventor: Morton Mernøe, Hoestvej 21, Charlotenlund DK-2920 (DK)

( * ) Notice: Subject to any disclaimer, the term of this patent is extended or adjusted under 35 U.S.C. 154(b) by 0 days.

(21) Appl. No.: 09/545,741

(22) Filed: Apr. 3, 2000

Related U.S. Application Data

(63) Continuation of application No. PCT/DK98/00457, filed on Oct. 21, 1998.

(30) Foreign Application Priority Data

Oct. 23, 1997 (DK) .................................................. 120697

(51) Int. Cl.[7] .................................................. A61M 37/00

(52) U.S. Cl. .......................................... 604/131; 604/122

(58) Field of Search .................................. 604/131, 132, 604/133, 138–141, 146, 147, 151–154, 65–67, 207, 236

(56) References Cited

U.S. PATENT DOCUMENTS

| | | | |
|---|---|---|---|
| 4,482,347 | 11/1984 | Borsanyi | 604/153 |
| 4,601,707 | 7/1986 | Albisser et al. | 604/131 |
| 4,756,706 | 7/1988 | Kerns et al. | 604/66 |
| 4,976,687 * | 12/1990 | Martin | 604/65 |
| 5,135,485 * | 8/1992 | Cohen et al. | 604/67 |
| 5,211,626 * | 5/1993 | Frank et al. | 604/65 |
| 5,632,606 * | 5/1997 | Jacobsen et al. | 417/415 |

FOREIGN PATENT DOCUMENTS

| | | | |
|---|---|---|---|
| 0062974 | 10/1982 | (EP) | A61M/5/14 |

* cited by examiner

*Primary Examiner*—Sharon Kennedy
*Assistant Examiner*—Ann Y. Lam
(74) *Attorney, Agent, or Firm*—Klein & Szekeres, LLP

(57) ABSTRACT

An infusion pump system comprises one or more infusion pump units and a stationary receptor system. Each unit comprises a housing of a size allowing the unit to be carried by a user as a portable unit and defining an exterior surface, a fluid inlet for establishing fluid communication from an external infusion bag, a fluid outlet for establishing fluid communication to an infusion site, a controllable pumping system having an inlet and an outlet, the inlet being connected to the fluid inlet and the outlet being connected to the fluid outlet for allowing transfer of fluid from the fluid inlet to the fluid outlet through activating the controllable pumping system, a first check valve provided at the inlet, a second check valve provided at the outlet, an electronic control means for controlling the operation of the pumping system and including at least two preset pumping programs for allowing the pumping system to be controlled in at least two alternative infusion pumping operations, and a power supply unit for supplying power to the pumping system and to the electronic control means and connectible through exterior terminals to external electric energy supply means. The receptor system includes a receptor for receiving the unit for maintaining the unit in a stationary mode and exposing the fluid inlet and fluid outlet and a mains supply unit for receiving electric energy from the mains supply and having terminals connectible to the exterior terminals for supplying electric energy to the power supply unit of the unit.

26 Claims, 15 Drawing Sheets

114 112 78 62 94 68 81 82 90 92 106 108 104 96 80 110 105 72 84 86 87 70 88 98 100 103 99 101 102 74 118 116 a
b
c
d
e
f
154
156
158
64
66
78
160
162
164
166
168
170
172
174
176
178
180
182
184
186
188
190
192
194
196
198
200
202
204
210
212
214
216
218
220
222
224
226
228
230
232
234
236
238
240
242
246
248
250
252
254
256
258
259
260

STANDBY MODE 1

Figure 10A:
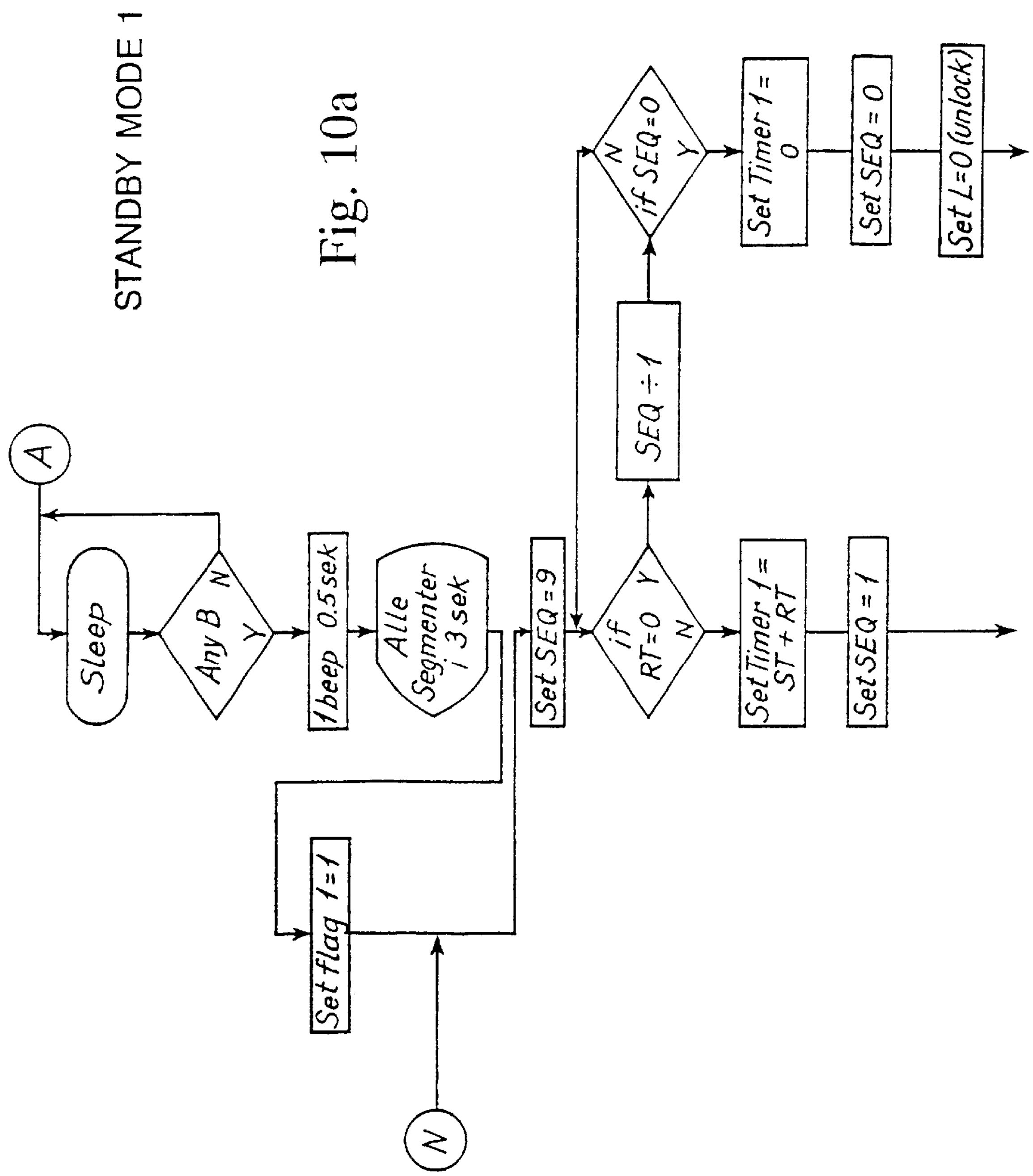
Figure 10B:
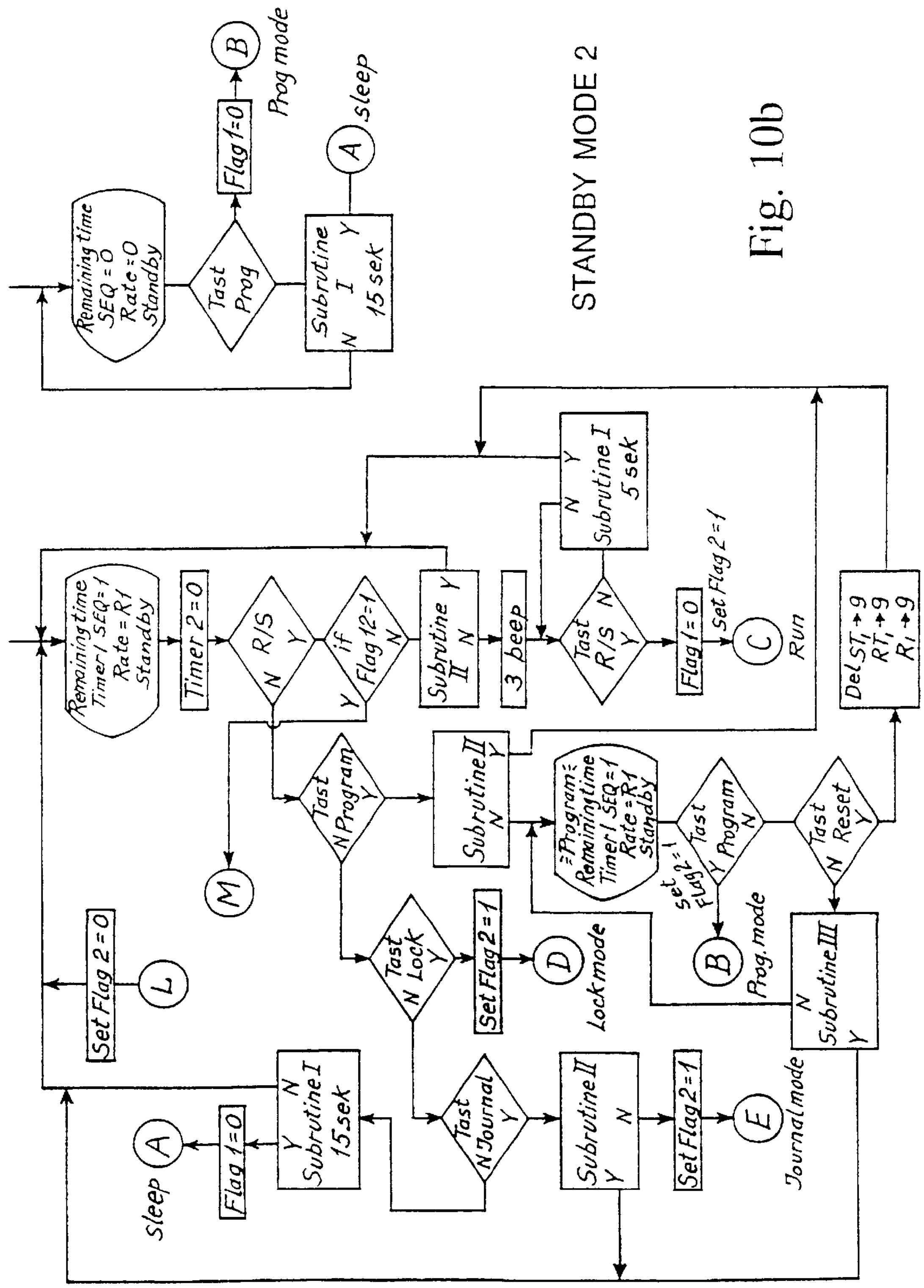
Figure 10C:
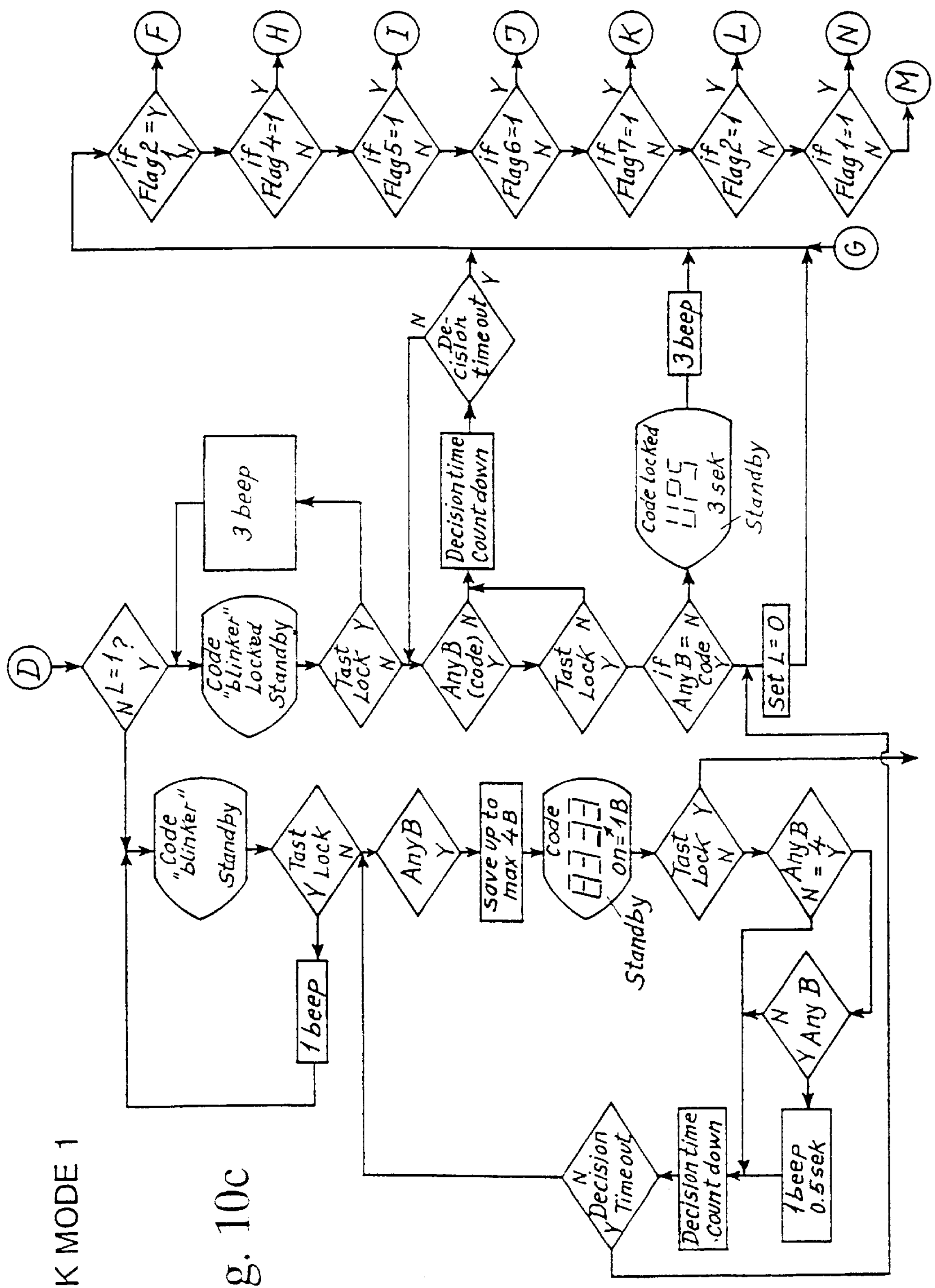
Figure 10D:
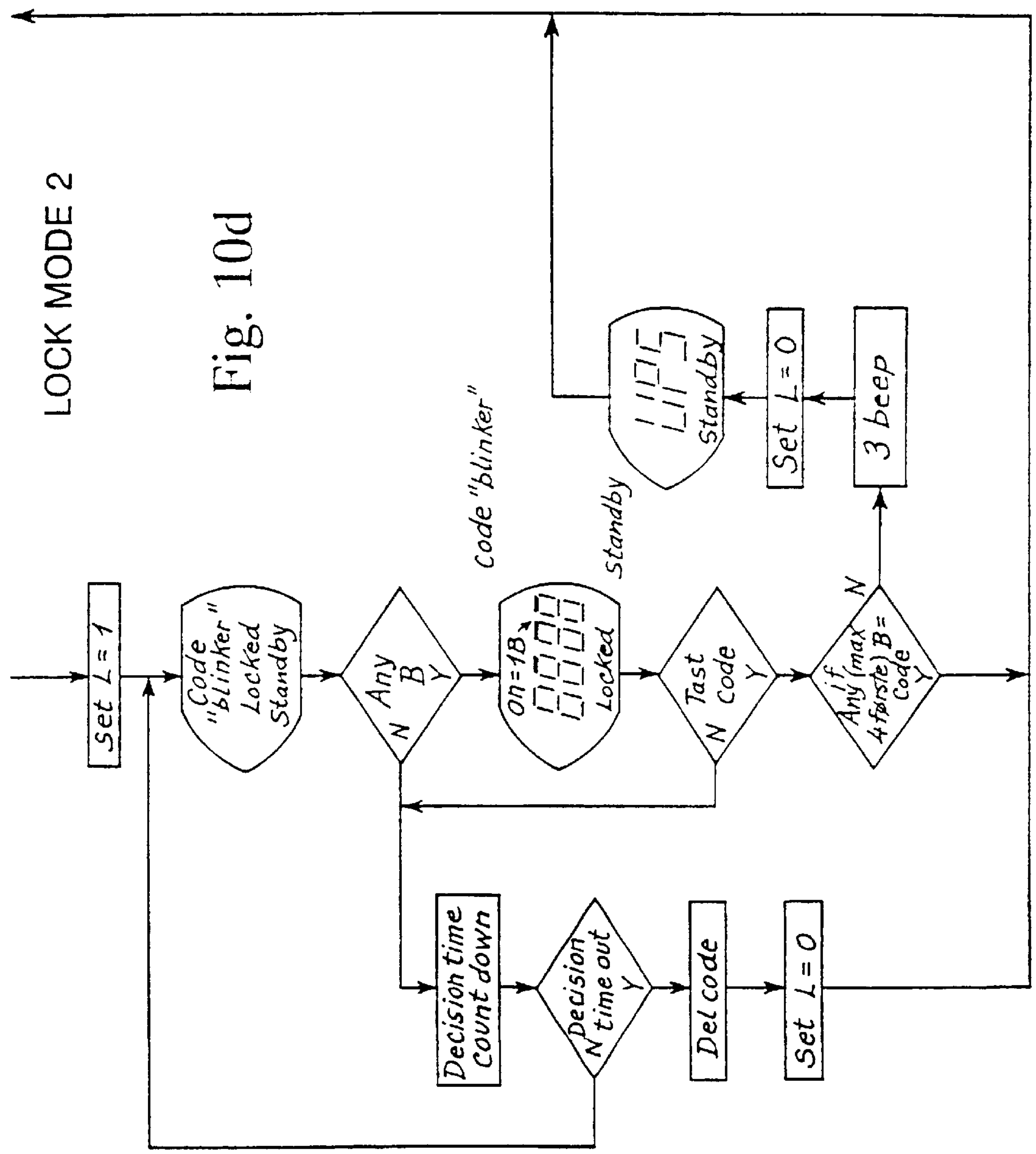
Figure 10F:
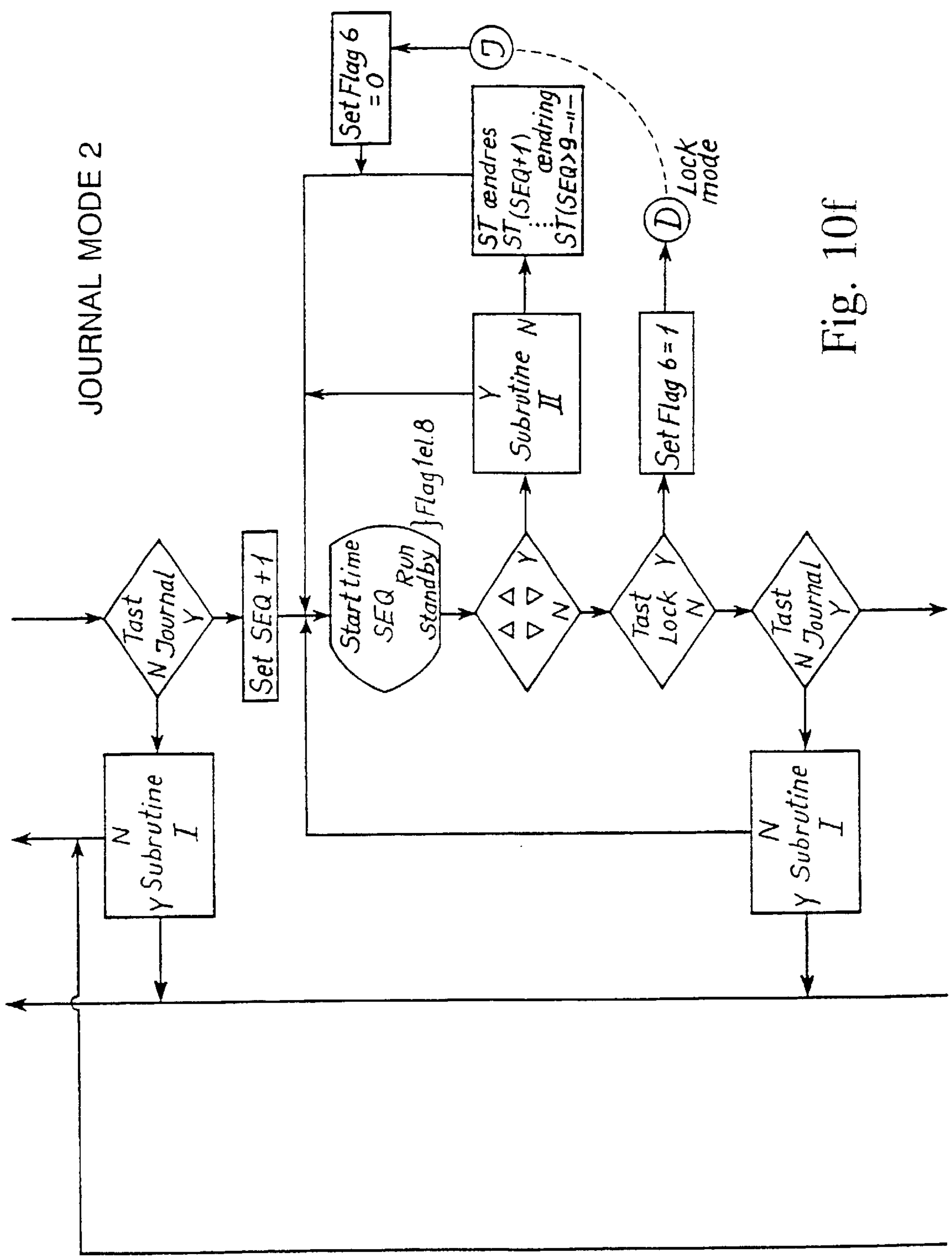
Figure 10G:
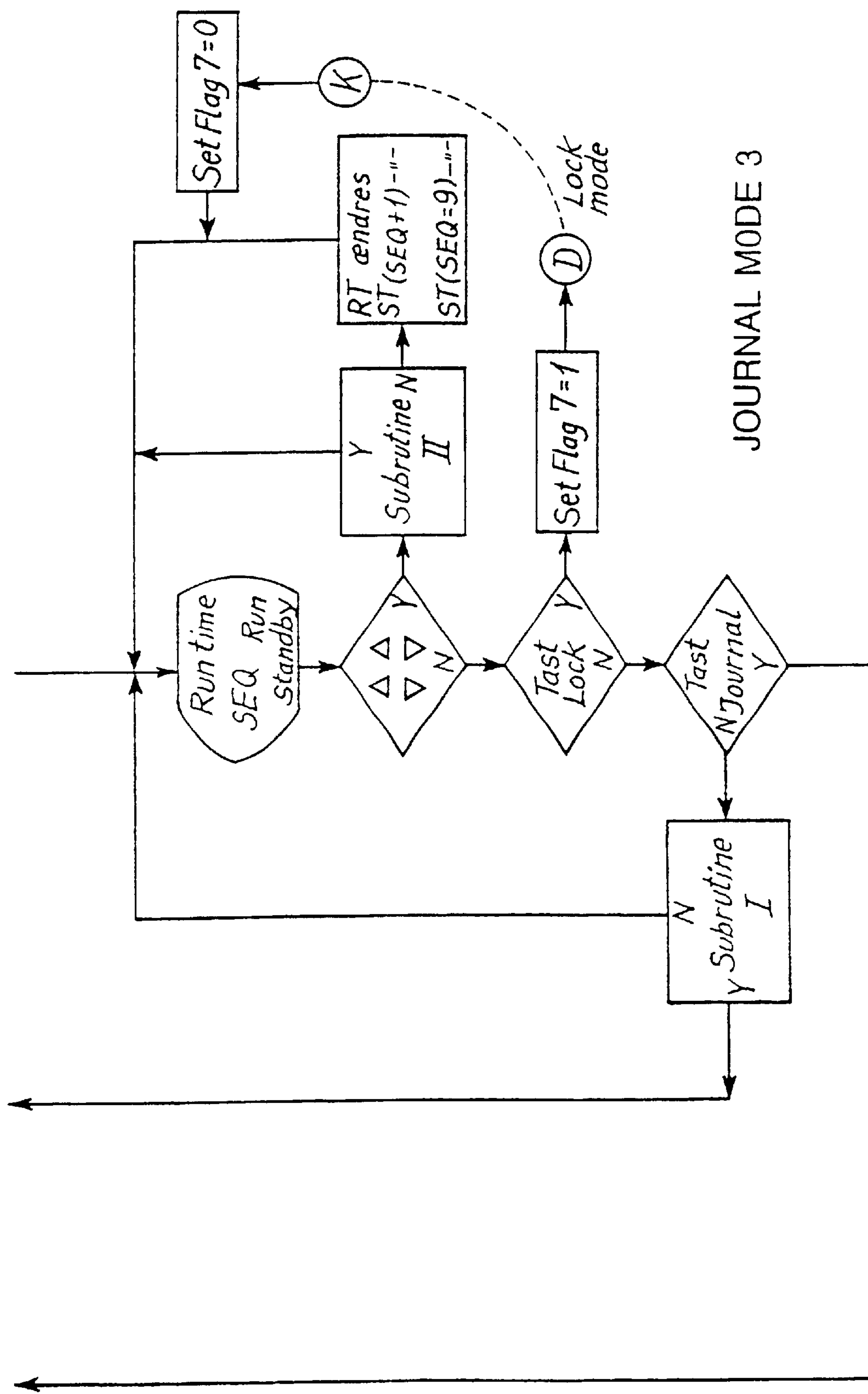
Figure 10H:
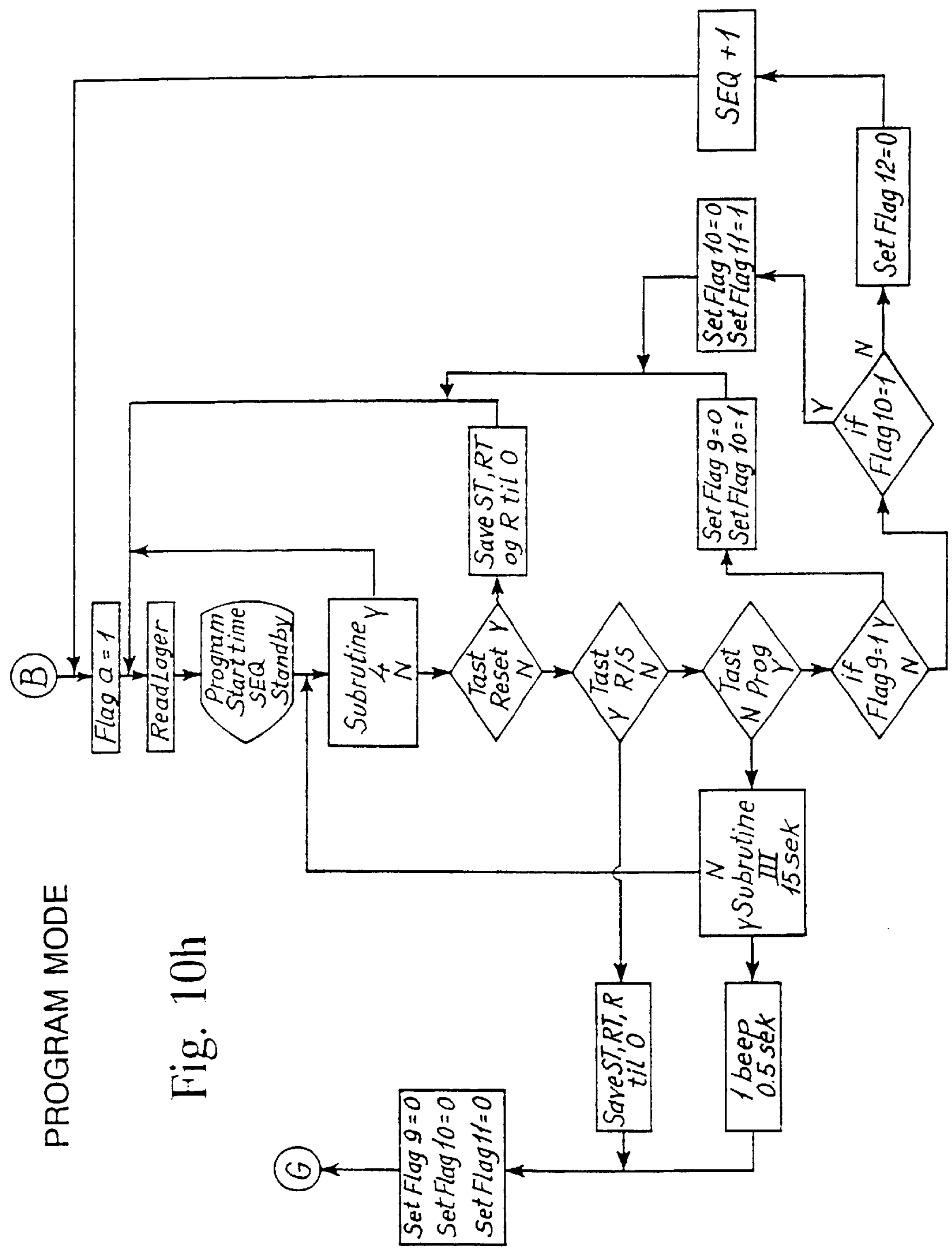
Figure 10I:
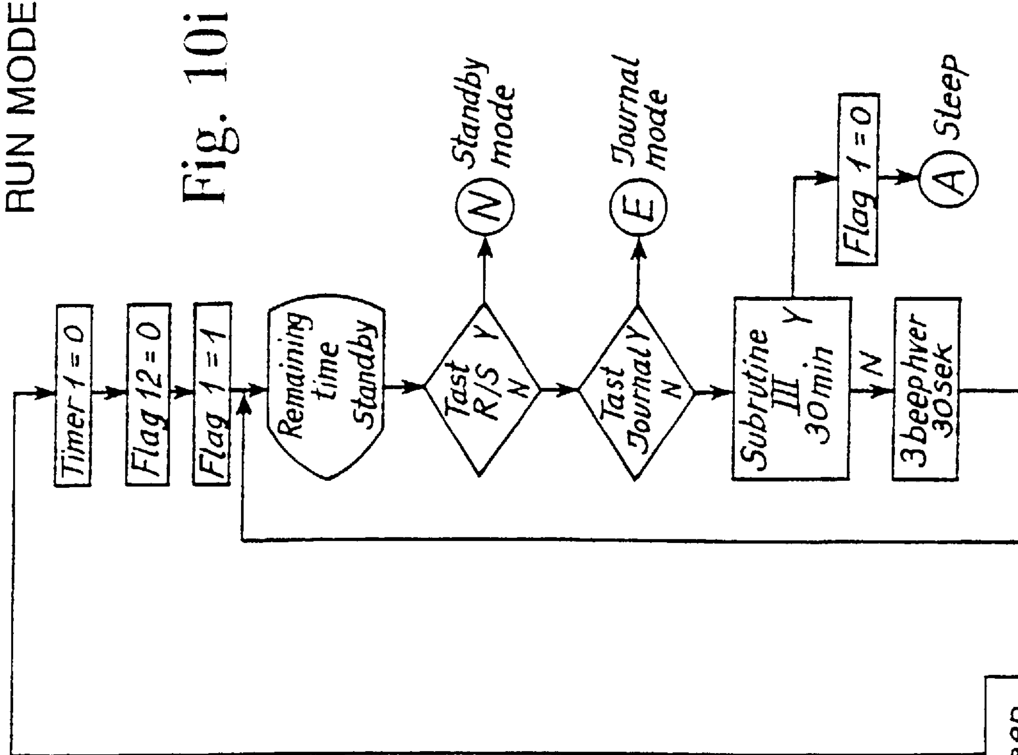
Figure 10I:
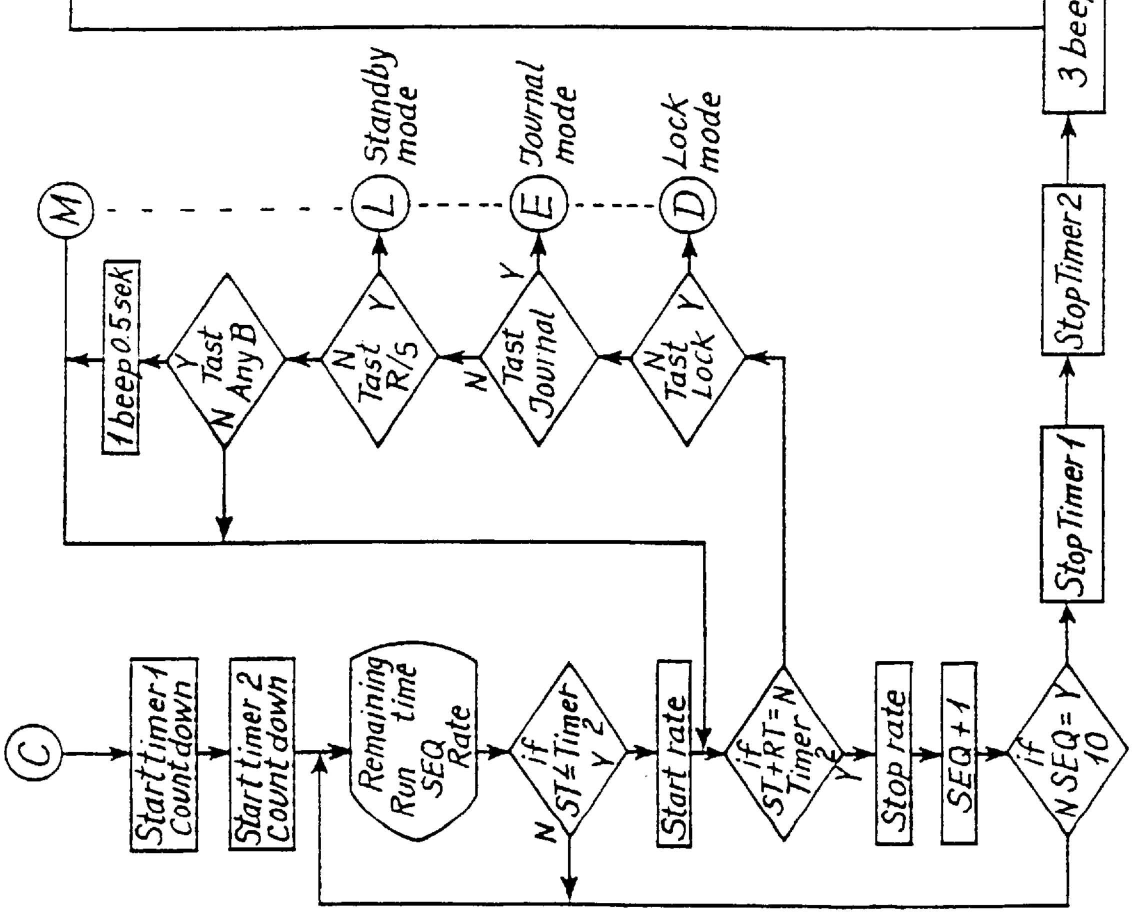

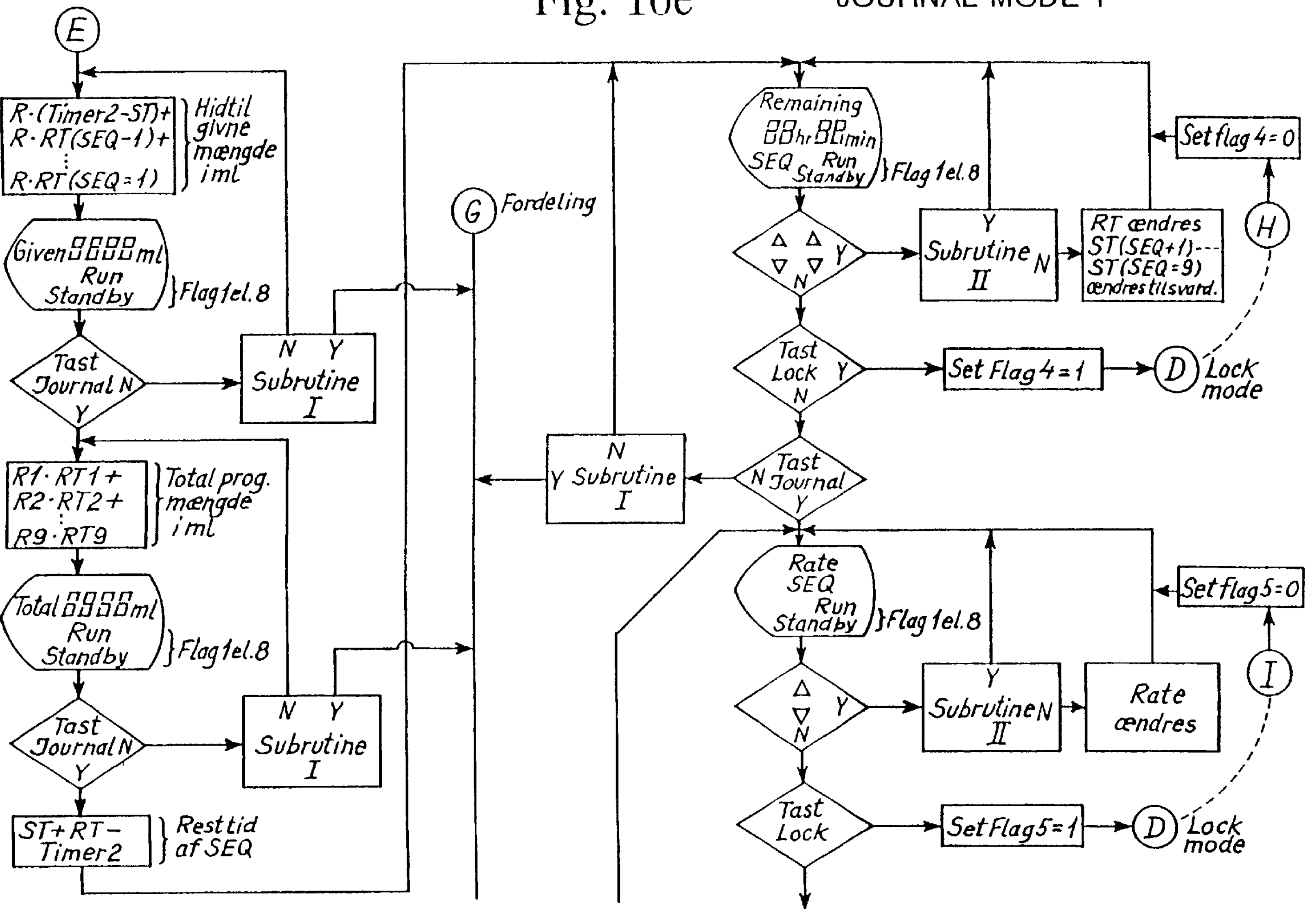
Fig. 10e
JOURNAL MODE 1
E
R·(Timer2-ST)+
R·RT(SEQ-1)+
R·RT(SEQ=1)
Hidtil givne mængde i ml
Given ml Run Standby
Flag1el.8
Tast Journal
Subrutine I
R1·RT1+
R2·RT2+
R9·RT9
Total prog. mængde i ml
Total ml Run Standby
Flag1el.8
Tast Journal
Subrutine I
ST+RT−Timer2
Rest tid af SEQ
G
Fordeling
Subrutine I
Remaining hr min SEQ Run Standby
Flag1el.8
Tast Lock
Tast Journal
Subrutine II
RT ændres
ST(SEQ+1)---
ST(SEQ=9)
ændres tilsvard.
Set Flag4=1
D
Lock mode
H
Set flag4=0
Rate SEQ Run Standby
Flag1el.8
Tast Lock
Subrutine II
Rate ændres
Set Flag5=1
D
Lock mode
I
Set flag5=0
Y
N

RUN MODE

INFUSION PUMP SYSTEM AND AN INFUSION PUMP UNIT

CROSS-REFERENCE TO RELATED APPLICATION

This application is a Continuation of co-pending International Application No. PCT/DK98/00457; filed Oct. 21, 1998.

The present invention generally relates to the technical field of infusing a liquid to a patient or person by means of an infusion pump, e.g. at a hospital. The present invention also relates to infusion of liquid to an animal. More precisely, the present invention relates to an infusion pump system and an infusion pump unit of a universal applicable structure for infusing a liquid into a patient or person.

At hospitals or nurse houses, it is often necessary to supply medication or body liquids to a person by means of an infusion pump in which instance the medication or the body liquids are infused into the body of the patient or person in question through a catheter which is connected to the blood transportation system of the patient or person, e.g. a vein or a venule. The usual technique of supplying medication by means of an infusion system to a patient or person involves the supply of physiologic liquid to the patient which physiologic volume is supplied at a specific rate and which serves as a diluting liquid as the medication is supplied to the physiologic liquid also at a specific rate such as one or two drops of medication per time period varying from a second or a few seconds to several minutes or even hours. The medication of a patient or person may in some applications involve the supply of the medication directly to the patient or person by means of the infusion pump.

Numerous infusion pumps and infusion pump systems are know in the art such as from U.S. Pat. No. 4,087,864, U.S. Pat. No. 5,222,946, published international patent application WO821/4399, German published patent application DE-OS 28 32 800, published international patent application WO93/10830, U.S. Pat. No. 5,316,452, U.S. Pat. No. 4,080, 967, U.S. Pat. No. 3,990,444, published British patent application GB 2,009,453, U.S. Pat. No. 4,443,216, U.S. Pat. No. 4,447,233, U.S. Pat. No. 5,167,631, U.S. Pat. No. 5,472,317, European patent No. 0 553 313, Danish patent 153,587 and Danish patent 167,037. Reference is made to the above published patent applications and patents and the above mentioned U.S. patents are hereby further incorporated in the present specification by reference.

Generally, the prior art infusion pumps are adapted to provide a specific function such as supplying a specific amount of liquid at a fixed rate. Also the prior art infusion pump systems generally constitute stand-alone apparatuses which are configurated as main supply apparatuses or alternatively battery powered apparatuses necessitating that a patient which is presently lying in a bed and receives medication by means of a main powered infusion pump needs to have the infusion pump substituted or at least disconnected from the main supply for a period of time provided the patient or person is to be moved from one location to another e.g. within the hospital or has to have the main powered infusion pumps substituted by a battery powered infusion pump provided the patient from being lying in the bed is to move around for exercising.

It is an object of the present invention to provide an infusion pump system allowing the patient or person using the infusion pump system according to the present invention to shift from a position sitting or lying in a bed and move around without necessitating the substitution or shift of the stationary infusion pump to a portable infusion pump as the infusion pump system according to the present invention constitutes a universally applicable or combined portable and stationary infusion pump system.

An advantage of the present invention relates to the fact that the infusion pump system according to the present invention may be used in different pumping modes as the infusion pump system includes several programmes for different operational modes and further preferably includes input means for input of different operational programmes.

The above object, the above advantage together with numerous other objects, advantages and features which will be evident from the below detailed description of presently preferred embodiments of the infusion pump system according to the present invention are in accordance with the teachings of the present invention obtained by an infusion pump system comprising:

at least one infusion pump unit, comprising:

a housing of a size allowing said infusion pump unit to be carried by a user as a portable infusion pump unit, said housing defining an exterior surface, a fluid inlet provided accessibly at said exterior surface for establishing fluid communication from an external infusion bag to said fluid inlet, a fluid outlet provided accessibly at said exterior surface for establishing fluid communication to an infusion site, a controllable pumping system included within said housing and having an inlet and an outlet, said inlet being connected to said fluid inlet and said outlet being connected to said fluid outlet for allowing transfer of fluid from said fluid inlet to said fluid outlet through activating said controllable pumping system, a first check valve provided at said inlet of said controllable pumping system, a second check valve provided at said outlet of said controllable pumping system, an electronic control means received within said housing for controlling the operation of said controllable pumping system, said electronic control means including at least two preset pumping programs for allowing said controllable pumping system to be controlled in at least two alternative infusion pumping operations, and a power supply unit housed within said housing for supplying power to said controllable pumping system and to said electronic control means and connectible through exterior terminals provided at said exterior surface of said housing to external electric energy supply means, a stationary receptor system including:

a receptor means for receiving and fixating said at least one infusion pump unit therein so as to maintain said at least one infusion pump unit in a stationary mode and exposing said fluid inlet and fluid outlet of said at least one infusion pump unit for allowing access thereto, and a mains supply unit for receiving electric energy from the mains supply and having terminals connectible to said exterior terminals for supplying said electric energy to said power supply unit of said at least one infusion pump unit, said mains supply unit constituting said external electric supply means.

According to the basic realization of the present invention, the infusion pump system according to the present invention comprises an infusion pump unit including a power supply unit for supplying electric power to the controllable pumping system of the infusion pump unit and further a stationary receptor means system including a main supply unit for supplying electric energy from the main supply to the power supply unit of the infusion pump unit. According to the basic teachings of the present invention, the controllable pumping system of the infusion pump unit includes electronic control means allowing the controllable pumping system to be operated in accordance with at least two different preset pumping programmes for modifying the operation of the infusion pump unit to a specific application.

The infusion pump unit of the infusion pump system according to the present invention may in accordance with the presently preferred embodiment of the infusion pump system according to the present invention be embodied as a microprocessor based infusion pump unit. Consequently, the electronic control means of the infusion pump unit may according to the presently preferred embodiment be constituted by a microprocessor control means allowing the microprocessor control means to firstly control the controllable pumping system and secondly control the overall operation of the infusion pump unit including the power supply unit. The microprocessor based infusion pump unit of the infusion pump system according to the present invention preferably further comprises a display means included in the electronic control means for displaying the operational mode of the infusion pump unit and further including keyboard means for addressing the electronic control means which are preferably constituted by the microprocessor control means.

According to a further modified and presently preferred embodiment of the infusion pump system according to the present invention, the keyboard means cooperating with the electronic control means of the infusion pump unit may be adapted to allow the electronic control means to be programmed for programming a specific pumping program into the electronic control means preferably constituted by the microprocessor control means for controlling the controllable pumping system to perform said specific pumping operation corresponding to said specific pumping programme.

Apart from the keyboard means preferably adapted to programme the electronic control means of the infusion pump unit, the electronic control means which are preferably constituted by the above described microprocessor control means may additionally or alternatively be programmable through an external programme port such as a conventional parallel or serial input/output port e.g. an RS232 port.

Additionally or alternatively, the electronic control means of the infusion pump unit of the infusion pump system according to the present invention may be preprogrammed allowing the infusion pump unit to be readily used for specific preset pumping operations corresponding to the preprogrammed pumping programmes of the electronic control means.

The check valves of the infusion pump unit of the infusion pump system according to the present invention may in accordance with a first embodiment be constituted by preset check valves. According to the presently preferred embodiment of the infusion pump system, at least one of the check valves, preferably the second check valve, is constituted by a controllable check valve for shifting the controllable check valve between a first active state and a second non-active state allowing the infusion pump unit to be modified from an infusion pump unit including two check valves into an infusion pump including a single check valve as the two check valve infusion pump unit is established provided the controllable check valve is in the above first active state whereas the single check valve infusion pump unit is established provided the controllable check valve is in the second non-active state.

The controllable check valve controllable between the first active state and the second non-active state may be configurated or embodied in numerous embodiments, however the non-active state is according to the presently preferred embodiment of the infusion pump unit of the infusion pump system according to the present invention established by means of a bypass valve establishing in a bypass mode a bypass of the controllable check valve and establishing in the bypass mode the second non-active state of the controllable check valve.

The overall pumping operation of the infusion pump of the infusion pump system according to the present invention is as indicated above established by the controllable pumping system which according to the presently preferred embodiment of the infusion pump unit of the infusion pump system according to the present invention includes a reciprocating plunger pump, the operation frequency of which is controllable from the electronic control means for altering the fluid transfer rate of the controllable pumping system.

In order to control the overall operational mode of the infusion pump unit, the infusion pump unit preferably further includes at least a first capacity detector circuit for detecting the presence of infusion liquid or alternatively air within the pumping system in order to allow the electronic control means to block the operation of the infusion pump unit of the infusion pump system provided air is detected within the pumping system. It is a well known fact within the art that infusion pump systems should under no circumstances introduce air bobbles into the blood transfusion system of the patient or person being medicated by means of the infusion pump system as the presence of air within the blood transportation system of the patient or person may cause a serious danger of injuries to the patient or person.

According to the presently preferred embodiment of the infusion pump unit of the infusion pump system according to the present invention, the first capacitive detector circuit comprises a capacitive attenuator including a variable capacitor communicating with said pumping system, said capacitive attenuator being supplied with an alternating input signal for generating an alternating output signal including an amplitude modulated component which is detected by an amplitude demodulator circuit.

The infusion pump unit of the infusion pump system according to the present invention preferably further includes a second capacitive detector circuit supplementing the first capacitive detector circuit of the infusion pump unit of the pumping system. Preferably the second capacitive detector circuit is embodied in accordance with the presently preferred embodiment of the first capacitive detector circuit and preferably, consequently, comprises a capacitive attenuator including a variable capacitor communicating with said pumping system, said capacitive attenuator being supplied with an alternating input signal for generating an alternating output signal including an amplitude modulated component which is detected by an amplitude demodulator circuit. The presence of two capacitive detector circuits within the infusion pump unit of the infusion pump system according to the present invention allows the operation of the pumping system to be controlled and monitored at two specific locations such as at the inlet and the outlet of the infusion pump unit ensuring a high degree of safety to the infusion pump system.

The reciprocating plunger pump of the controllable pumping system of the infusion pump unit of the infusion pump system according to the present invention may be embodied in accordance with numerous pump techniques, however, for providing a pumping system in which the risk of generating cavities within the pumping system or excessive pressure load to the pumping system alternatively, which in both instances might be hazardous to the patient or person receiving medication from the infusion pump system and at the same time provide a controllable pumping system the operational mode of which is easily monitored, the reciprocating plunger pump of the infusion pump unit of the infusion pump system according to the present invention preferably includes a solenoid attenuator and a mechanical attenuator for providing mechanical attenuation of solenoid activated plunger of the plunger pump.

The above object, the above advantage together with numerous other objects, features and advantages which will be evident from the below detailed description of the infusion pump system according to the present invention is in accordance with the teachings of the present invention also obtained by an infusion pump unit comprising

- a housing of a size allowing said infusion pump unit to be carried by a user as a portable infusion pump unit, said housing defining an exterior surface,
- a fluid inlet provided accessibly at said exterior surface for establishing fluid communication from an external infusion back to said fluid inlet.
- a fluid outlet provided accessibly at said exterior surface for establishing fluid communication to an infusion site,
- a controllable pumping system included within said housing and having an inlet and an outlet, said inlet being connected to said fluid inlet and said outlet being connected to said fluid outlet for allowing transfer of fluid from said fluid inlet to said fluid outlet through activating said controllable pumping system,
- a first check valve provided at said inlet of said controllable pumping system,
- a second check valve provided at said outlet of said controllable pumping system,
- an electronic control means received within said housing for controlling the operation of said controllable pumping system, said electronic control means including at least two preset pumping programs for allowing said controllable pumping system to be controlled in at least two alternative infusion pumping operations, and
- a power supply unit housed within said housing for supplying power to said controllable pumping system and to said electronic control means and connectible through exterior terminals provided at said exterior surface of said housing to external electric energy supply means, and
- to be used in connection with a stationary receptor system including:
  - a receptor means for receiving and fixating said at least one infusion pump unit therein so as to maintain said at least one infusion pump unit in a stationary mode and exposing said fluid inlet and fluid outlet of said at least one infusion pump unit for allow in access thereto, and
  - a mains supply unit for receiving electric energy from the mains supply and having terminals connectible to said exterior terminals for supplying said electric enter to said power supply unit of said at least one infusion pump unit, said mains supply unit constituting said external electric supply means.

Figures 1, 2:
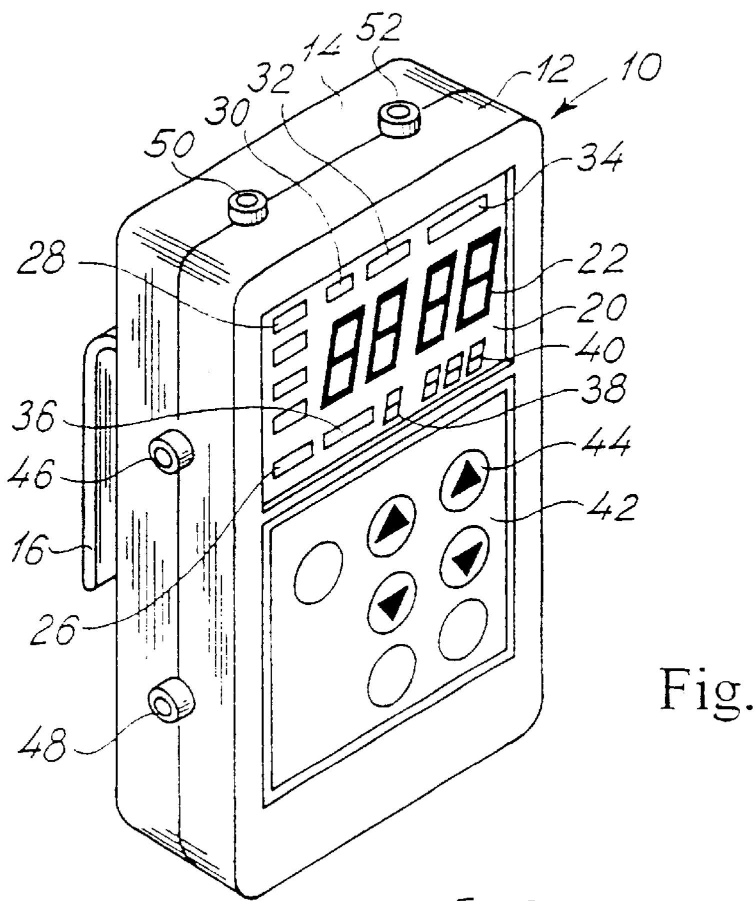
Figure 4:
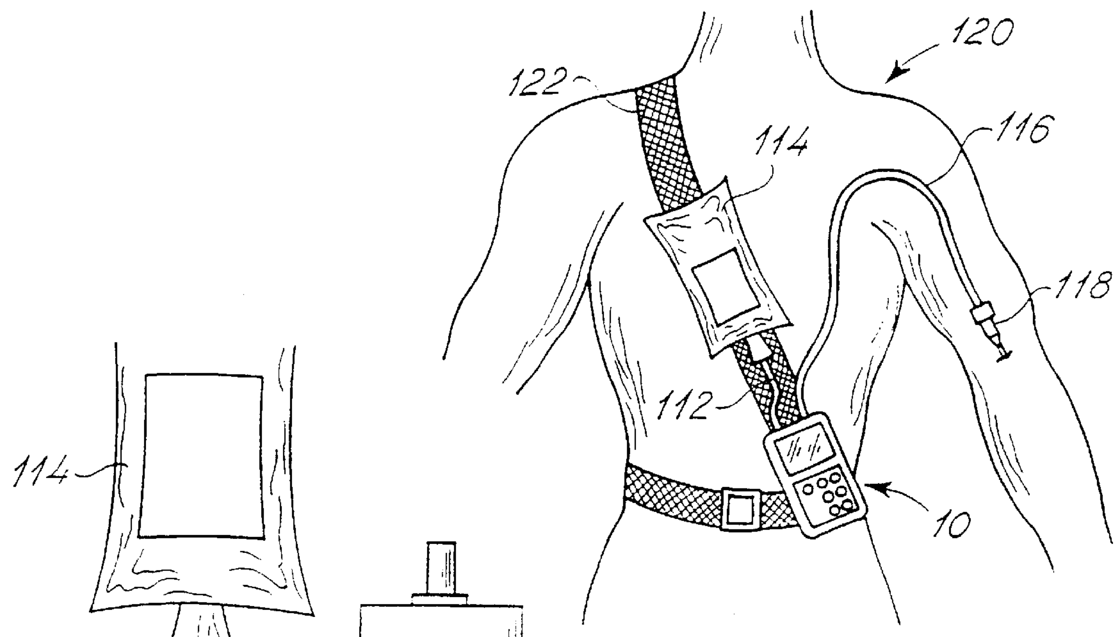
Figure 3:
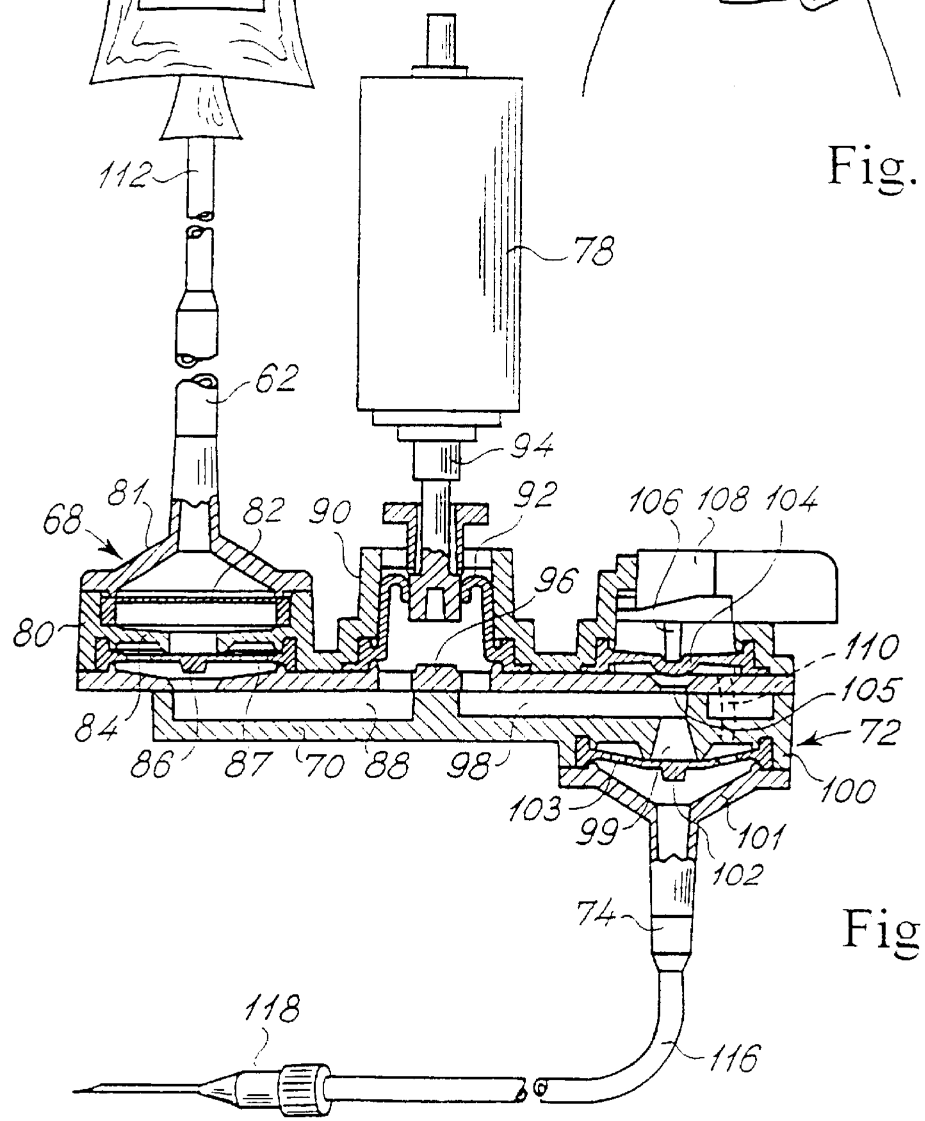
Figure 5:
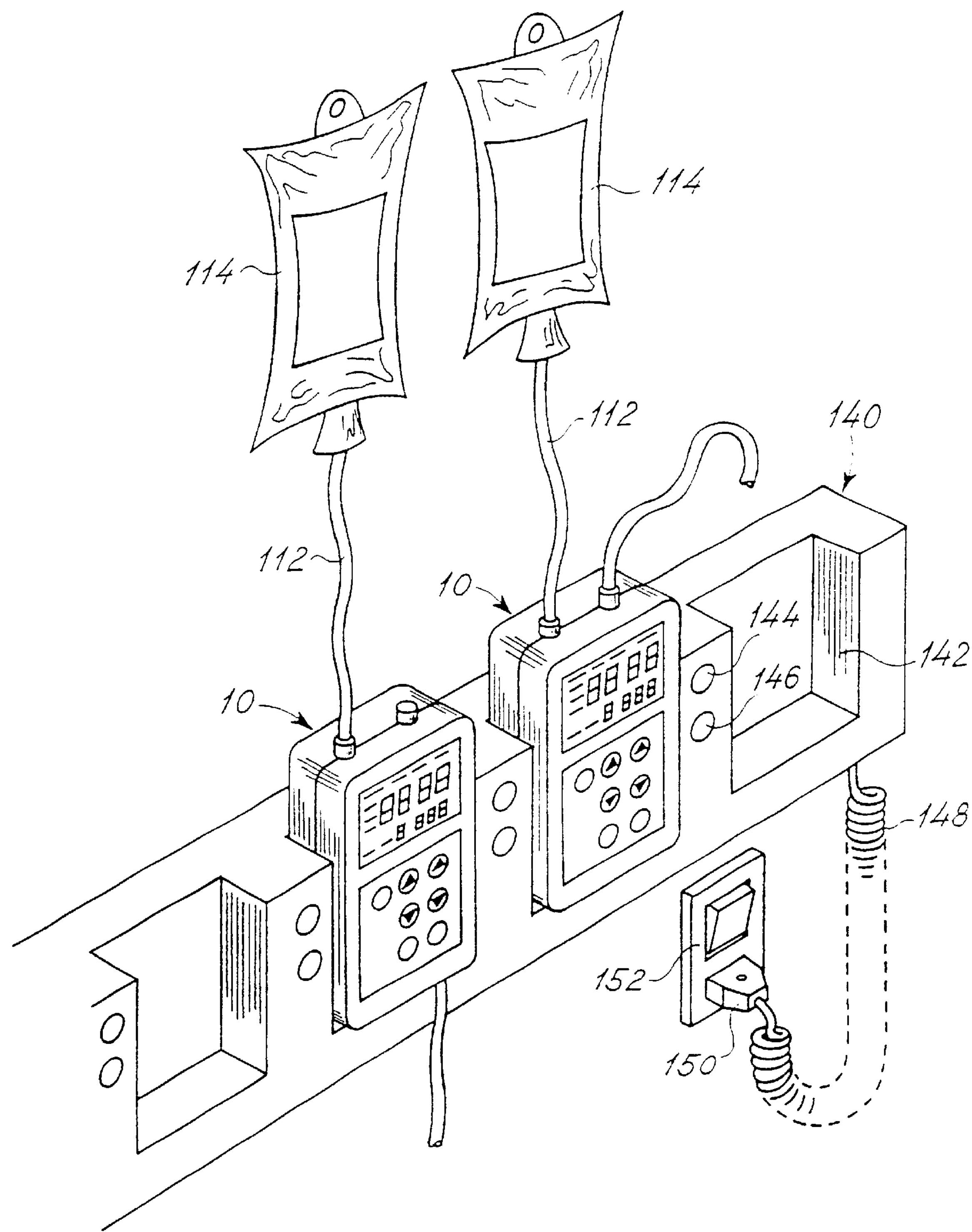
Figure 6:
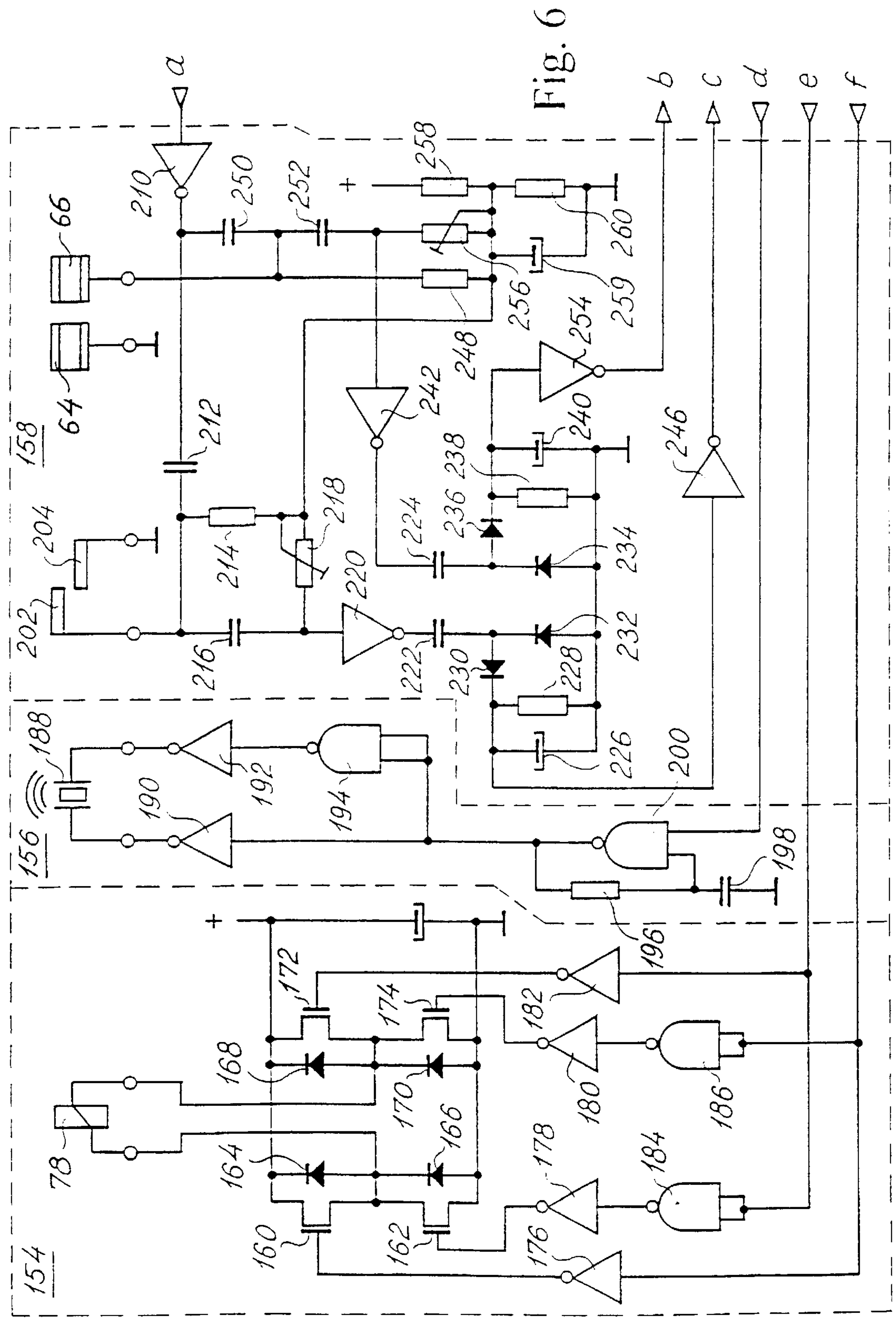
Figure 7:
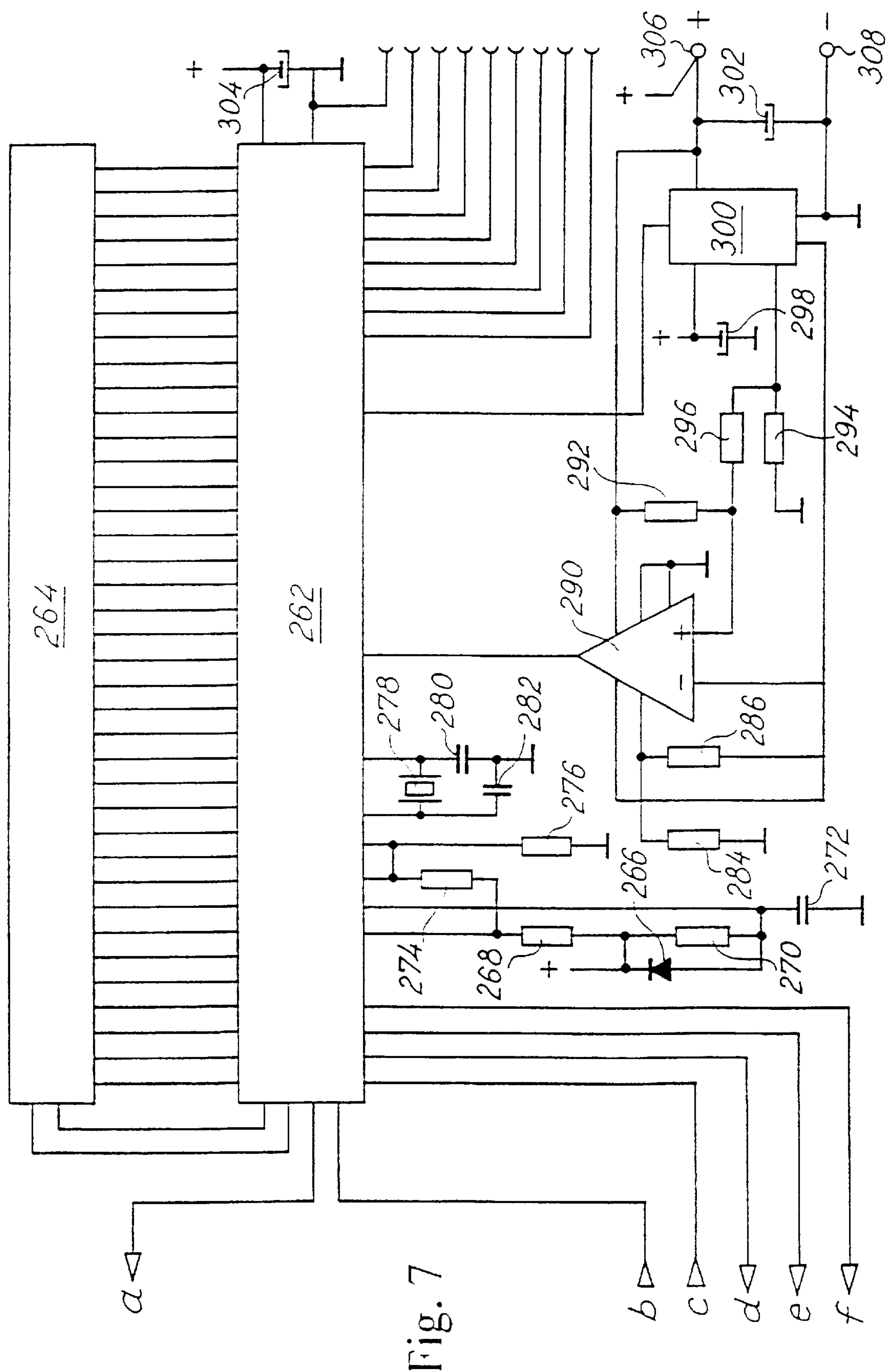
Figure 8:
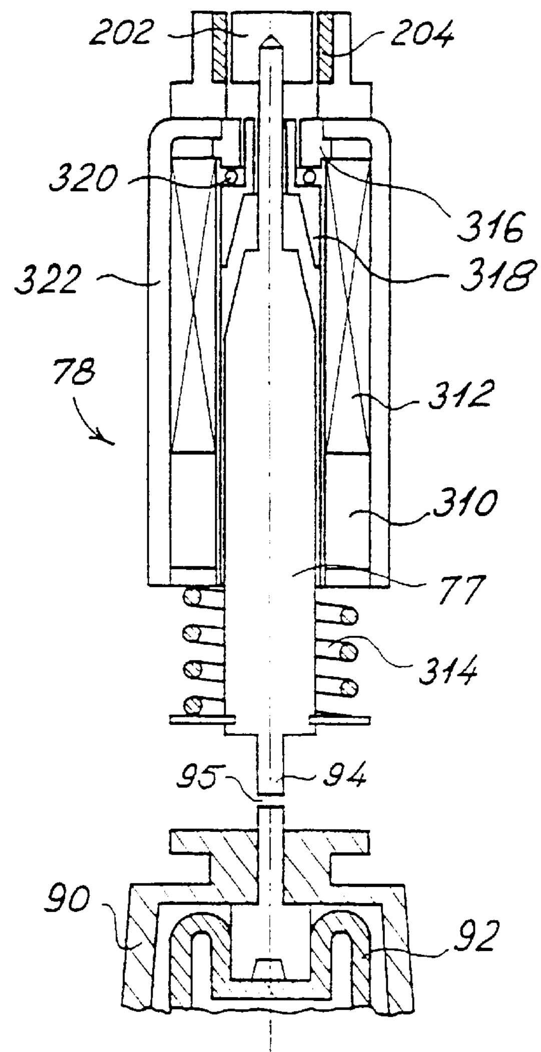
Figure 9:
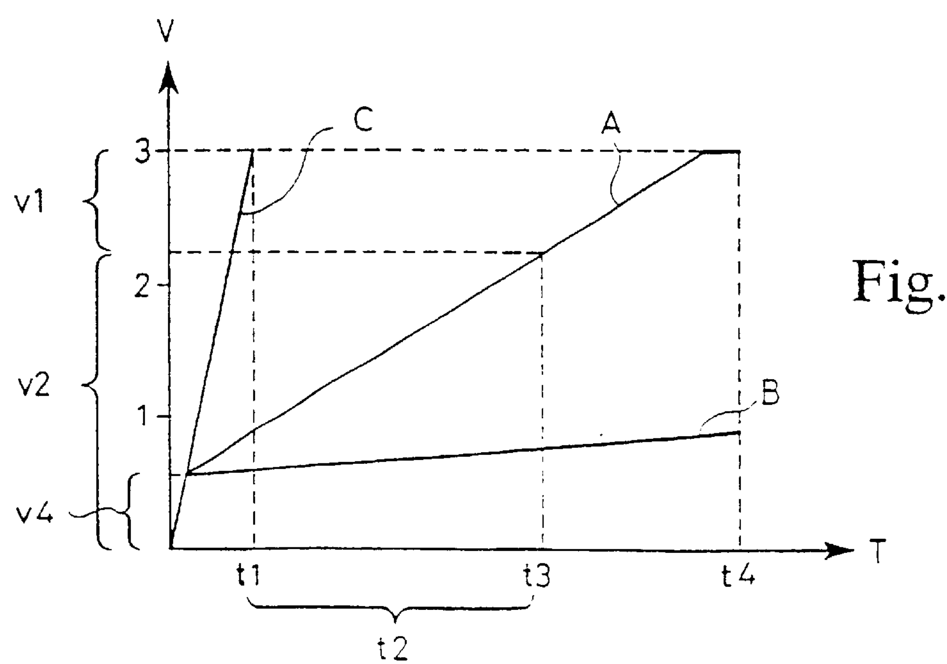

The invention is now to be further described with a reference to the drawings in which FIG. 1 is a perspective and schematic view of a first and presently preferred embodiment of a portable infusion pump unit according to the present invention, FIG. 2 is an elevational and sectional view of the first embodiment of the portable infusion pump unit illustrated in FIG. 1, FIG. 3 is a schematic view of the interior of the first embodiment of the portable infusion pump unit illustrated in FIGS. 1 and 2, disclosing the flow path thereof, FIG. 4 is a schematic view illustrating a possible application of the first embodiment of the portable infusion pump unit illustrated in FIGS. 1, 2 and 3, FIG. 5 is a perspective and schematic view illustrating the application of the first embodiment of the portable infusion pump unit illustrated in FIGS. 1–4 in a stationary charger and fixation system for providing a stationary infusion pump system, FIG. 6 is a diagrammatic view of a first part of the electronic circuitry of the first embodiment of the portable infusion pump unit illustrated in FIGS. 1–4, FIG. 7 is a diagrammatic view of a second part of the electronic circuitry of the first embodiment of the portable infusion pump unit illustrated in FIGS. 1–4, FIG. 8 is a schematic and vertical sectional view of a plunger component included in the first embodiment of the portable infusion pump unit illustrated in FIG. 1, FIG. 9 is a diagram illustrating the plunger stroke versus time of the plunger component illustrated in FIG. 8 in three alternative operational modes, and FIGS. 10*a*–10*i* are diagrammatic views of 9 alternative operational modes illustrated in flow diagrams.

In the drawings, a first and presently preferred embodiment of a portable infusion pump unit or apparatus is disclosed designated the reference numeral 10 in its entirety. The apparatus 10 comprises a housing composed of two shell-like housing parts 12 and 14 constituting a front and rear housing part, respectively. The front an rear housing parts 12 and 14, respectively, are easily disassembled allowing the user to obtain access to the interior of the apparatus for substituting an interior fluid passage component to be described in greater detail below with reference to FIG. 3 constituting a disposable pre-sterilized component which is easily demounted after use and readily replaced prior to use. From the rear side of the housing part 14, a clip 16 allowing the apparatus 10 to be fixed to a strap or a belt extends. It is to be realised that terms such as upper, lower, front, rear, etc., unless otherwise stated, in the present context define positions or orientations determined by the intentional application of the apparatus 10 as the apparatus is positioned in an upright and substantially vertical position, e.g. received in the belt of a user by means of the clip 16 or otherwise positioned exteriorly or non-implantatedly relative to the user.

In the front housing part 12, a display 20 is provided, comprising two sets of two digits designated the reference numerals 22 and 24, respectively, for displaying digits representing the time lapsed or the time remaining for infusion operation expressed in minutes and hours, respectively, or seconds and minutes, respectively, or alternatively for displaying digits representing the supply of infusion liquid as expressed in volume per time unit, e.g. ml per hour. The display 20 further includes a display area 26 for informing the user and/or a person operating the infusion pump apparatus 10 or nursing the user regarding the operational mode of the apparatus, such as standby or running information. Furthermore, the display 20 includes a number of individual displays positioned above one another and above the standby/running display 26, one of which is designated the reference numeral 28. These individual displays 28 are adapted to display information such as the operational mode, e.g. the information that the apparatus is in a program mode, information regarding whatever information is presented on the two-digit displays 22, 24, such as the time remaining for infusion operation, the total time of the infusion operation, whether or not the apparatus is running or is to be started, or any other relevant information to be presented to the user or operator. The display 20 further includes three individual alarm displays 30, 32 and 34 for informing the user of the presence of air in the infusion pump circuitry, pressure fault or failure or low battery, respectively. A further display 36 informs the user or operator of the program sequence presently used or programmed, which program sequence is represented by a digit displaced by a 1-digit display 38. A 3-digit display 40 of the display 20 represents information to the user or operator regarding the infusion supply measured in ml per hour or similar relevant measure or ratio.

Below the display 20, a keyboard 42 is provided including a set of keys, one of which is designated the reference numeral 44 for allowing the user/operator to control the portable infusion pump unit 10 to perform a specific operation or to program the apparatus by shifting between specific program sequences by increasing a specific digit displayed in a 1-, 2- or 3-digit display, such as the displays 22, 24, 38 and 40, by increasing or reducing the digit in question and by shifting a cursor route relative to the various individual displays of the display 20 for allowing the user/operator to modify the operational mode or shift between various preset programs of the apparatus.

At the one side wall of the housing, composed by the housing parts 12 and 14 of the unit or apparatus 10, two terminals 46 and 48 are provided for allowing the apparatus 10 to be connected to an electronic charger for supplying electric power to an internal rechargeable battery pack or cell of the apparatus. The terminals 46 and 48 may alternatively or additionally serve as input/output terminals for establishing communication between the apparatus 10 and an external apparatus or equipment such as an external data logging apparatus or surveillance apparatus or further alternatively for communicating with an external processing unit such as a personal computer or data logging apparatus. Still further, the apparatus 10 may be provided with a conventional input/output terminal such as a conventional RS 232 terminal for establishing communication between the apparatus 10 and an external computer such as the above-mentioned personal computer for processing data produced by the apparatus concerning the operational mode of the apparatus and also supplementary data produced by the apparatus or auxiliary equipment, e.g. data representing the temperature of the infusion liquid supplied by the apparatus 10 or data supplied by additional external measuring or surveillance equipment. In the top wall of the housing of the apparatus 10 two recesses are provided for receiving two tube connectors 50 and 52 constituting a fluid inlet and a fluid outlet, respectively, of the above-mentioned fluid passage component to be described in further detail below with reference to FIG. 3. As is evident from FIG. 2, a further fluid outlet 54 is provided in the bottom wall of the housing of the apparatus 10 opposite to the fluid outlet 52.

In FIG. 2, the interior structure of the portable infusion pump unit or apparatus 10 is disclosed, illustrating the fluid inlet 50 and the fluid outlets 52 and 54. In FIG. 2, the reference numerals 56 and 58 designate two printed circuit boards including the electronic circuitry of the apparatus to be described in further detail below with reference to FIGS. 6 and 7 and including the display, the rechargeable power pack or cell circuitry and the CPU-circuitry of the apparatus controlling the overall operation of the apparatus including the infusion operation. Alternatively, the electronic circuitry of the apparatus may be included in a single printed circuit board or, alternatively, three or more printed circuit boards. The internal rechargeable battery pack or cell is designated the reference numeral 60.

In FIG. 2, the internal flow system of the portable infusion pump apparatus 10 is disclosed, constituting a disposable and replaceable fluid passage component as mentioned above and including an inlet tube 62 connected to the fluid inlet 50. Two capacitive detectors 64 and 66 are mounted on the inlet tube 62 and communicate with the electronic circuitry of the apparatus housed on the printed circuit board 56 and 58 for detecting presence of air bobbles if any in the infusion liquid input to the fluid inlet 50. At its output end, the inlet tube 62 communicates with a first check valve 68 which constitutes an inlet to a pump housing component 70, in which an internal fluid passage is provided, as will be described in greater details below with reference to FIG. 3, which fluid passage terminates in an output or second check valve 72 from which two branched-off outlet tubes 74 and 76 communicate with the fluid outlets 54 and 52, respectively. For transferring the infusion liquid or any other liquid input to the portable infusion pump unit 10 through the fluid inlet 50 to an application site through one of the fluid outlets 52 and 54, a piston type pump 78 is provided. The internal flow system of the portable infusion pump comprising the fluid inlet 50, the inlet rube 52, the capacitive detectors 64 and 66 belonging to the inlet tube 62, the first check valve 68, the pump housing component 70, the output check valve 72, the outlet tubes 74 and 76, and the outlets 52 and 54 constitute an integral disposable and replaceable fluid passage component to be described in greater detail below with reference to FIG 13

In FIG. 3, the interior of the check valves and also the pump housing component 70 is disclosed in greater detail. The first check valve 58 basically comprises a central circular cylindrical housing component 80 from which a frustro-conical top part 81 extends upwardly communicating with the inlet tube 62 and arresting an inlet filter element 82 at the transition between the frustro-conical top part 81 and the cylindrical housing component 80. The cylindrical housing component 80 comprises a central annular oral component 84 which is sealed off in the initial or non-active position by a downwardly deflectable sealing membrane 86. Provided the pressure below the sealing membrane 86 is lower than the pressure above the membrane 86, the membrane 86 is forced downwardly allowing liquid to pass through the central aperture of the central annular component 84 and further through apertures 87 provided offset relatively to the centre of the sealing membrane 86.

The first check valve 68 communicates with an inlet passage 88 of the pumping house component 70 terminating in an inner chamber defined within an upwardly protruding annular top housing component 90 in which a reciprocating plunger 94 of the piston pump 78 is movable in the direction to and from an abutting pin 96 which separates the inlet passage 88 from an outlet passage 98. The interspace between the reciprocating plunger of the piston pump 78 and the inner surface of the annular top housing component 90 is sealed by means of a highly flexible sealing gasket 92.

The outlet passage 98 communicates with the above described second check valve 72 which is basically of a configuration similar to and functioning as a check valve similar to the above described first check valve 58, however differing from the above described first check valve in that the second check valve 72 does not include any filter element similar to the filter element 82. The second check valve 72 includes a downwardly protruding annular housing part 100, which is cast integral with the pumping house component 70, fulfilling, however, the same purpose as the above described annular housing part 80 of the first check valve. From the annular housing part 100, a downwardly protruding frustro-conical housing part 101 similar to the above described frustro-conical housing part 81 extends communicating with the outlet tube 74 and similarly the outlet tube 76 described above with reference to FIG. 2. Within the annular housing part 100, a sealing membrane 102 similar to the above described sealing member 86 is received, which includes apertures 103 similar to the apertures 87 described above. The sealing membrane 102 communicates with a conical bore 99 communicating with the outlet passage 98 for sealing off communication from the outlet passage 98, through the conical bore 99 to the outlet tube 74 provided the sealing membrane 102 rests against an abutting lower surface defining the lower boundary of the conical bore 99.

The pumping operation of the portable infusion pump unit 10 is established as follows. Initially, the first check valve 68 and the second check valve 72 are in their initial and sealing positions. It is also assumed that liquid is present within the inlet tube 62 within the inlet passage 88 and the outlet passage 98 and also within the outlet tube 74. The piston pump 78 is activated through the supply of an electric signal such as an alternating electric signal or a pulsed signal causing a solenoid within the piston pump to move the reciprocating plunger 94 upwardly or downwardly. The piston pump 78 is preferably, as will be described in greater detail below with reference to FIG. 8, a piston pump in which the plunger 94 is biassed by means of a spring towards the exterior in relation to the housing of the piston pump and, consequently, downwardly in relation to the orientation of the piston pump 78 shown in FIG. 3. The piston pump includes a bi-stable solenoid cooperating with the biassing spring of the piston pump for producing a controlled movement on the one hand generating adequate activation of the check valves 68 and 72 and at the same time preventing the generation of excessive pressure fluctuations within the pumping house component 70.

Assuming that the first movement of the reciprocating plunger 94 is in movement upwardly, a relative vacuum is created within the inlet passage 88 and the outlet passage 98 by the increase of the volume defined below the sealing gasket 92. Through the creation of the relative vacuum within the inlet passage 88, the first check valve 68 is operated as the downwardly deflectable sealing membrane 86 is caused to move downwardly allowing liquid to flow into the inlet channel 88 through the central aperture of the central annular component 84 as described above. At the same time, the relative vacuum within the outlet passage 98 creates a relative vacuum above the sealing membrane 102 which is biassed so as to prevent free flow through the second check valve 72 urging or forcing the sealing membrane into sealing off and abutting engagement with a wall part circumferentially encircling and defining the conical bore 99, and consequently preventing liquid from being transferred from the outlet passage 98 to the outlet tube 74. In summary, during the raising of the reciprocating plunger 94, the first check valve 68 is activated and caused to open whereas the second check valve 72 is blocked.

As the reciprocating plunger is moved downwardly, a relative increased pressure is created within the inlet passage 88 and the outlet passage 98 and the operations of the first and second check valves are shifted as the relative increased pressure within the inlet passage 88 causes the first check valve 68 to block and seal off whereas the increased pressure within the outlet passage 98 causes the second check valve 72 to open allowing the fluid present within the outlet passage 98 to be forced out through the conical passage 99, through the apertures 103 of the sealing membrane 102 and further into the outlet tube 74. The rate of transfer and consequence the flow of liquid from the outlet tube 74 is controlled by the rate of operation of the piston pump 78 as an increased frequency of reciprocating the reciprocating plunger 94 increases the velocity of flow of fluid or liquid from the inlet tube 62 to the outlet tube 74.

Above the second check valve 72, a bypass valve is provided, comprising a sealing membrane 104 which is acted upon by a central stem element 106 of a turnable knob 108 so as to force the sealing membrane 104 into sealing off and abutting engagement with a conical bore 105 provided above and in registration with the above described conical bore 99. Provided the conical bore 105 is sealed off by means of the sealing membrane 104, the bypass valve is not in operation. Provided the sealing membrane 104 is raised from its sealing off and abutting engagement with the conical bore 105 as the knob 108 is rotated for causing elevation of the actuator stem 106, communication from the outlet passage 98 is established through a bypass passage 110, bypassing the communication from the outlet passage 98 through the conical passage 99 for allowing fluid to flow from the outlet passage 98 through the bypass passage 110 and further through the apertures 103 of the sealing membrane 102 which is consequently not functioning as the bypass valve is in operation.

The piston pump 78, which may constitute a replaceable component of the portable infusion pump unit or apparatus 10, may provide a specific stroke and, consequently, a specific flow volume per stroke. Therefore, the piston pump 78 is preferably provided with a switch or actuator cooperating with a switch of the electronic circuitry of the apparatus for informing the microprocessor of the electronic circuitry of the apparatus of the type of piston pump included within the apparatus at present. The technique of providing information to the microprocessor concerning the type of piston pump included within the apparatus at present may be established by means of numerous techniques well-known in the art per se such as by means of code switches, optic capacitive or inductive readers, or simply by means of a feedback circuit monitoring the work rate of the piston pump.

In FIG. 3, an inlet tube 112 is shown establishing communication from the inlet tube 62 through the fluid inlet 50 not shown in FIG. 3, however, shown in FIG. 2 from an infusion bag 114 which may constitute an infusion bag including an infusion liquid simply constituting physiological liquid or additionally or alternatively a drug suspended in any appropriate liquid, or alternatively blood plasma. The outlet from the outlet tube 74 of the portable infusion pump unit 10 shown in FIG. 4 is connected to an outlet tube 116 through the fluid outlet 54, not shown in FIG. 3, however, shown in FIG. 2, which external outlet tube 116 communicates with a cannular assembly 118 of a basically conventional structure.

The inlet tube 112 and the outlet cube 116 may constitute separate inlet and outlet tubes to be connected to the infusion pump unit 10 through the inlet and outlet 50 and 52 or, alternatively, 54, respectively. Alternatively, and preferably, the inlet tube 112 and the outlet tube 116 constitute integral components of the disposable and replaceable fluid passage component illustrated in FIG. 3, which fluid passage component is cooperating with and activated by means of the piston pump 78. Further alternatively, the infusion bag 114 may be configurated and housed within a container component which is configurated so as to allow the infusion bag 114 to be received and supported on top of the infusion pump unit or apparatus 10 as the above-mentioned receiver is simply connected to and supported by the housing of the portable infusion unit or apparatus 10.

The infusion of liquid from the infusion bag 104 is further illustrated in FIG. 4, in which the portable infusion pump 10 is received and fixed relative to an individual 120 by means of a belt or strap 122 on which the infusion bag 114 is further fixated. In FIG. 4, the external inlet tube 112, the external outlet tube 116 and the cannular assembly 118 are also illustrated.

In FIG. 5, the above described first and presently preferred embodiment of the portable infusion pump unit or apparatus 10 is shown in duplicate received within a stationary receptor 140 in which a plurality of receptor compartments 142 are defined. Each of the receptor compartments 142 is provided with a set of charger terminals for establishing electrical conductive communication with the charger terminal 46 and 48 of the apparatus or unit 10 received within the receptor compartment 140 in question for charging the internal rechargeable battery pack or cell of the apparatus or unit through the supply of electric energy from a mains power supply unit of the receptor assembly 140 which mains supply power supply unit receives electric power through a coiled mains supply wire 148 terminating in a mains plug 150 which is received in a mains AC outlet socket 152.

The receptor assembly 140 further includes a set of indicator lamps 144 and 146. Provided none of the indicator lamps 144 and 146 corresponding to a specific receptor compartment 142 are turned off, the indication informs the user or operator that no charging is taking place in the receptor compartment in question. Provided a portable infusion pump unit is received within a specific receptor compartment 142, one of the lamps 144 and 146 corresponding to the receptor compartment is turned off, one of which informs the user or operator that the protable infusion pump unit in question is to be recharged, or alternatively the other lamp is turned on informing the user or operator that the portable infusion pump unit in question is fully charged and ready for use. Alternative information display modes, such as flashing of lamps for informing malfunction in the rechargeable battery pack or cell of the portable infusion pump is of course also readily deduceable.

In FIGS. 6 and 7, the electronic circuitry of the above described first and presently preferred embodiment of the portable infusion pump unit 10 according to the present invention is shown. In FIG. 6, a first part of the electronic circuitry is shown, which part further includes three subsections 154, 156 and 158. The subsection 154 constitutes a driver section for driving the piston pump 78 and receives an oscillating driver signal through two terminals e and f which are supplied through a set of gates 176, 178, 180, 182, 184 and 186 to gate terminals of respective power MOS-FETs 160, 162, 172 and 174, the source and drain terminals of which are protected through protective diodes 164, 166, 168 and 170, respectively. The power MOS-FETs 160, 162, 172 and 174 constitute a complementary bridged driver circuit.

The second subsection 156 constitutes an alarm section in which a piezoelectric alarm 188 is included. An alarm signal is received on a terminal d and input to a NAND gate 200 which is connected in a auto-feedback mode through a resistor 196 and a capacitor 198 and the output of which is connected to two driver gates 190 and 192 one of which is further in a complementary operational mode supplied through a NAND gate 194.

The third subsection 158 comprises two detector circuits each including two sets of capacitive detectors 64, 66 and 202, 204, respectively. The capacitative detectors 64 and 66 serve the purpose of detecting the presence of any air bobbles within the inlet tube 62 of the portable infusion pump unit 10, whereas the capacitive detectors 202 and 204 serve the purpose of monitoring the position and the movement of the plunger 94 of the piston pump 78. The detector circuits included in the third subsection 158 further comprise a gate 210 receiving a control signal from the central CPU of the apparatus to be described below with reference to FIG. 7 and supplies the control signal to the capacitive detector 202 through a capacitor 212 and also supplies the control signal to the capacitive detector 64 through a capacitor 250. The first detector circuit further comprises a capacitor 216 and the second detector section similarly comprises a capacitor 252. The capacitive detectors 202 and 204 together constitute a capacitor which is connected in a series configuration with the capacitor 212 and, consequently, constitutes a capacitive attenuator in relation to the control signal output from the gate 210. The attenuation of the control signal output from the gate 210 is detected by a gate 220 constituted by an inverter which is connected to the node of the capacitor 212 and the capacitor constituted by the capacitive detectors 202 and 204 through the capacitor 216.

As mentioned above, the capacitive detectors 202 and 204 constitute a variable capacitor serving as a detector element. As the plunger is in its bottom position, the reactants of the variable capacitor constituted by the capacitive detectors 202 and 204 is low. Provided the plunger is in its top position, the capacitive detectors 202 and 204 are spaced apart producing a larger reactant. The amplitude of the signal detected by the inverter 220 may be altered by means of a resistive attenuator comprising a series configuration of a variable resistor 218 and a fixed resistor 214. The output of the inverter 220 is connected through a capacitor 222 to a conventional AM detector circuit comprising a capacitor 226, a resistor 228 and to diodes 230 and 232. The AM detector circuit is of a configuration commonly used within AM radio detectors. The AM detector circuit is connected to a further inverter 246 supplying the demodulated output signal generated by the AM detector circuit to the central CPU of the electronic circuitry to be described below with reference to FIG. 7.

The second detector circuit part of the third subsection 158 similarly comprises a capacitor 252 corresponding to the capacitor 216 described above for presenting a signal to the input of a further inverter 242 corresponding to the inverter 220 described above which signal is generated by the variable attenuator comprising the series configuration of the capacitor 250 and the capacity detectors 64 and 66 which together constitute a viable capacitor the reactance of which is low provided liquid is present within the inlet tube 62 and the capacitance of which is high provided air bubbles or air is present within the inlet tube 62. Similar to the variable attenuator described above, the second detector circuit comprises a set of resistors 248 and 256 constituting a fixed and a variable resistor, respectively. The output of the gate or inverter 242 is supplied to an AM detector circuit through a capacitor 224 which AM detector circuit comprises two diodes 234 and 236 corresponding to the diodes 232 and 230, respectively, described above, a resistor 238 corresponding to the resistor 228 described above and a capacitor 240 corresponding to the capacitor 216 described above. The output of the AM detector circuit is connected to a further gate or inverter 254 which supplies a control signal representing the presence of air or alternatively liquid within the inlet tube 62 to the central CPU of the electronic circuitry to be described below with reference to FIG. 7.

As described above, the two detector circuit parts of the third subsection 158 are basically identical and a common resistive voltage divisor comprising two resistors 258 and 260 are included in the third subsection 158 for defining a preset voltage level above ground, however the positive supply voltage and representing the virtual series voltage level of the detector circuit part. The node of the resistors 258 and 260 is AC shunted by means of a capacitor 254. The positive voltage defined by the voltage divisor comprising the resistors 258 and 260 also serve the purpose of biasing the two detector circuit parts including the gates 220 and 242, respectively. The above described resistors shunting the capacitors constituted by the capacitive detectors 202, 204 and 64, 66 also serve the purpose of decoupling any static positive and negative voltage generated across the variable capacitors constituted by the capacitive detectors 202 204, and 64, 66, respectively. As will be understood, the resistor 214 and 248 of the first detector circuit part and the second detector circuit part, respectively, serve the purpose of providing static decoupling of the variable capacitors of the detector circuit part in question. The variable resistors 218 and 256 serve the dual purpose of providing sensitivity adjustment facility and of transferring the virtual zero level or bias voltage to the inputs of the gates 220 and 242, respectively. In general, the detector circuit parts initially provide a differentiation of the control signal input to the detector circuit part in question and thereupon provides an variable attenuation of the input signal. The variable attenuation of the differential input signal is detected by means of the individual detector circuit part.

In FIG. 7, a second part of the electronic circuitry is shown constituting the central CPU and display section. Centrally, the second part of the electronic circuitry comprises a CPU 262 including integral display driver circuitry for driving an electronic block 264 constituting the display 20 described above with reference to FIG. 1. The CPU 262 is connected to peripheral components constituting the supply and clock driver circuitry of the CPU. Consequently, the CPU 262 is connected to a crystal 278 generating the clock frequency of the CPU and the basic control frequency of the overall apparatus. Furthermore, the CPU 262 is connected to a voltage regulator circuit 300 which receives a voltage across input terminals 306, 308 which are decoupled by a capacitor 302. An output terminal of the voltage regulator block 300 is connected to a capacitor 298 defining the positive supply rail of the overall circuitry. The voltage regulator block 300 is further connected to a comparator circuit constituted by an operation amplifier 290 which is connected with peripheral resistors 292, 294 & 296 for supplying a reference signal representing the state of the battery supply or the rechargeable battery package or cell of the apparatus which signal is input to the CPU 262 for informing the CPU of low battery state of the rechargeable pack or cell. The CPU also generates the signals constituting control signals which are supplied to the above described first part of the electronic circuitry which control signals are supplied on the terminals a, d, e & f and receives control signals on the terminals b & c from the above described first part of the electronic circuitry of the apparatus. No further description of the electronic circuitry is being made, as the electronic circuitry per se is constituted by a microprocessor based technique well known in the art per se. Reference is made to the below example in which the individual components of the electronic circuitry are identified.

In FIG. 8, the piston pump 78 is shown in greater details. The piston pump 78 centrally includes a movable magnetic core 77 which at its lower end is connected to the plunger 94 and at its upper end connected to the capacitive detector 202 which cooperates with the attenuated capacitive detector 204 in the variable capacitive detector circuit described above with reference to FIG. 6. The movable magnetic core 77 is housed within a magnetic circuit comprising a permamagnet 310 and a solenoid coil 312. The movable magnetic core 77 is further acted upon by a bias spring 314 which serves the purpose of forcing the movable magnetic core 77 to its bottom position. The magnetic circuit comprising the permamagnet 310 and the solenoid coil 312 cooperates with the movable magnetic core 77 by means of a magnetic conductive yoke 322 which magnetic circuit also includes the movable magnetic core 77. The magnetic circuit further includes a top pole piece including two separate segments 316 and 318 which are internally mechanically stationary by means of an O-ring 320. As the solenoid coil 312 is energized, the movable magnetic core 77 is moved upwardly causing the magnetic circuit to be shorted. As the solnoid coil 312 is deenergized, the bias spring 314 causes the movable magnetic core 77 to move downwardly as the magnetic circuit is opened. The reference numeral 95 designates an air cap between the lower end of the plunger 94 through which air gap the plunger 94 acts on the piston of the piston pump 78 and more precisely the piston acting on the flexible sealing gasket 92 also shown in FIG. 3. The air gap 95 on the one hand allows the disposable and turnal?? flow system of the portable infusion pump to be removed and replaced provided the infusion unit 10 is shifted from one patient or person to another and on the other hand allow the plunger 94 to start moving after deenergizing the solenoid coil 312 before the motion of the plunger 94 is transferred into a pumping operation within the internal flow system of the infusion pump as will be illustrated in greater details in FIG. 9.

In FIG. 9, a diagram is known illustrating the dependency between the signal output by the inverter 246 to the central microprocessor of the electronic circuitry and time for three states of operation of the piston pump. A curve A illustrates the normal operational state of the piston pump in which state the inlet tube 62 is unblocked and filled with infusion liquid and in which the output tube 74 is also unblocked. A curve B represents an operational mode in which the outlet tube 74 is blocked and a curve C illustrates an operational mode in which the inlet tube 62 is blocked. Along the abscissa axis, the time lapses since the deactivation of the solenoid coil 312 is indicated from which time of deactivation of the solenoid coil 312, the bias spring 314 causes the plunger 94 to move downwardly. It is to be realized that a certain clearance of the order of 0.5 mm exists between the position of the plunger in which the solenoid coil 312 is energized and the position in which the plunger activates or engages with the top housing component 90 of the pumping house component 70.

At the time of deenergizing the solenoid coil 312, the capacitive detectors 202 and 204 are in the position positioned close to one another producing a low reactance capacitance as described above with reference to FIG. 6. Similarly, as the plunger 94 is in its bottom position, the capacitance of the capacitor constituted by the capacitive detectors 202 and 204 is high. Provided the normal operational state exist, the downwardly motion of the plunger 94 is subjected to certain mechanical resistance causing a certain delay in the shift of capacitance of the capacitor constituted by the capacitive detectors 202 and 204. Thereupon, the plunger moves fairly rapidly downwardly causing the generation of the response output from the inverter 246 corresponding to the curve A illustrated in FIG. 9. Provided the inlet tube 62 is blocked, vacuum is generated within the inlet tube, and the plunger 94 may move downwardly without any mechanical resistance causing the capacitance of the capacitor constituted by the capacitive detectors 202 and 204 to raise rapidly as indicated by the curve C in FIG. 9. Similarly provided the outlet tube 74 is blocked, the piston is exposed to extreme resistance preventing the plunger from being moved beyond a specific position as the infusion liquid is non-compressible. The response output from the inverter 246 therefore fails to raise above a specific level as indicated by the curve B in FIG. 9.

The central microprocessor of the electronic circuitry of the infusion pump unit 10 monitors the response output from the inverter 246 as the microprocessor after a period of time T1 monitors the response output from the inventor or gate 246. Provided the inlet tube 62 is blocked, the microprocessor detects a maximum response corresponding to the level V1+V2 indicated along the ordinate axis in FIG. 9. Provided a level exceeding the level V2 is not detected at the time T1, the microprocessor waits until the lapse of a further period of time T2 until the time T3 at which time the microprocessor detects whether or not the response has increased above the level or reached the level V2 indicated that the piston pump is operating in its normal operational mode. Provided the microprocessor after time T3 still has not detected a response of the order of V2, the microprocessor carries out a further detection at time T4 at which time the microprocessor provided the response still has not reached the level V2 determines that the outlet tube 74 is blocked. In FIG. 9, the level V4 corresponds to the response supplied from the inverter 246 as the plunger 94 is moved at distance corresponding to the above described clearance.

In FIGS. 10A–10I, specific flow diagrammatic illustrations of a total of 9 different operational modes of the infusion pump unit or apparatus are shown which flow diagrammatic charge are believed to be self-explanatory and therefore need no further comments or description.

EXAMPLE

The above described presently preferred and first embodiment of the portable infusion pump cell or apparatus 10 was implemented in a prototype embodiment by the below components. The housing was composed of two ABS housing parts 12 and 14. The terminals 46 and 48 were constituted by non-insulated female plugs allowing electrical connection to corresponding plugs or cooperating male plugs. The display 20 was implemented by individual display elements. The keyboard 42 was implemented by individual pushbutton keys.

The electronic circuitry of the portable infusion pump cell or apparatus 10 was implemented in accordance with the diagram described above with reference to FIGS. 6 & 7. The following components were used. Power MOS-FET 160 was a IRF 7304. The power MOS-FET 162 was an IRF 7301. The power MOS-FET 172 was a IRF 7304. The power MOS-FET 174 was a IRF 7301. The diodes 164, 166, 168 & 170 were constituted by individual shottky-diodes. The inverters 176, 178, 180 & 182 were constituted by single integrated circuits of the type 4504. The NAND gates 184 & 186 were implemented by a 4093. The inverters 190 & 192 were inverters implemented by a 4504. The NAND gates 194 & 200 were 4093. The resistor 196 was a IM. The capacitor 198 was 470 pF. The inverters 210, 220, 242, 244 & 246 were 40106. The diodes 230, 232, 234, 236 were IN4148. The capacitor 212 was 2.7 pF. The resistor 214 was IM. The adjustable resistor 218 was 10K. The capacitor 216 was 60 pF. The capacitor 22 was 10 nF. The capacitor 224 was 10 nF. The electrolytic capacitor 226 was 47 nF. The resistor 228 was 1 M Ω. The resistor 238 was 1 M Ω. The electrolytic capacitor 240 was 47 nF. The resistor 248 was 1 M Ω. The capacitor 250 was 2.7 pF. The capacitor 252 was 100 pF. The electrolytic capacitor 254 was 2.2 μF. The adjustable resistor 256 was 1 k Ω. The resistors 258 and 260 were 1 M Ω. The diode 266 was IN4142. The resistor 268 was 1 k Ω. The resistor 270 was 47 k Ω, the resistor 274 was 47 k Ω. The resistor 276 was 47 k Ω. The clock crystal 278 was 5 MHz. The capacitor 280 was 30 pF. The capacitor 282 was 30 pF. The resistor 284 was 2.4 M Ω. The resistor 286 was 10 k Ω. The operational amplifier 290 was M931. The resistor 292 was 4.3 M Ω. The resistor 294 was 1.2 M Ω. The resistor 296 was 10 k Ω. The electrolytic capacitor 298 was 2.2 μF. The voltage regulator block 300 was in integrated electronic circuit of the type M 883. The electrolytic capacitor 302 was 2.2 μF. The electrolytic capacitor 304 was 2.2 μF.

Although the invention has been described above with reference to presently preferred and advantageous embodiments of the infusion pump system and infusion pump unit according to the present invention, the infusion pump system and also the infusion pump unit may be modified in numerous ways obvious to a person having ordinary skill in the art without deviating from the scope of the present invention. In particular, the electronic circuitry of the infusion pump unit may be modified in numerous ways by e.g. combining or separating various components of the electronic circuitry such as through combining the electronic clock circuits of the electronic circuitry into a single clock circuitry or by including individual or respective electronic clock circuits of the individual blocks of the electronic circuitry. Thus, the subsection 158 illustrated in FIG. 6 may comprise a separate clock circuitry generating a clock signal substituting the clock signal as illustrated in FIG. 6 and generated by the CPU 252 illustrated in FIG. 7. Also the subsection 154 may be modified by including a power MOSFET protecting circuitry eliminating the risk of simultaneously triggering the power MOSFETs of the two branches at the same time and thereby eliminating the risk of destroying the power MOSFET unintentionally. Alternatively, the power MOSFETs may be substituted by planar power transistors well known in the art or any other power driver circuit. A further modification of the above described preferred and advantageous embodiment of the infusion pump may be established by including a purge function in the apparatus allowing the user to manually activate the infusion pump for providing an increased infusion dose. The above modifications are of course to be construed part of the present Invention as defined in the appending claims.

What is claimed is:

1. An infusion pump system, comprising:

at least one infusion pump unit, comprising:

a housing of a size allowing said infusion pump unit to be carried by a user as a portable infusion pump unit, said housing defining an exterior surface, a fluid inlet provided accessibly at said exterior surface for establishing fluid communication from an external infusion bag to said fluid inlet, a fluid outlet provided accessibly at said exterior surface for establishing fluid communication to an infusion site, a controllable pumping system included within said housing and having an inlet and an outlet, said inlet being connected to said fluid inlet and said outlet being connected to said fluid outlet for allowing transfer of fluid from said fluid inlet to said fluid outlet through activating said controllable pumping system, a first check valve provided at said inlet of said controllable pumping system, a second check valve provided at said outlet of said controllable pumping system, an electronic control means received within said housing for controlling the operation of said controllable pumping system, said electronic control means including at least two preset pumping programs for allowing said controllable pumping system to be controlled in at least two alternative infusion pumping operations, a power supply unit housed within said housing for supplying power to said controllable pumping system and to said electronic control means and connectible through exterior terminals provided at said exterior surface of said housing to external electric energy supply means, and a first capacitive detector circuit for detecting the presence of infusion liquid or alternatively air within the pumping system; and a stationary receptor system including:

a receptor means for receiving and fixating said at least one infusion pump unit therein so as to maintain said at least one infusion pump unit in a stationary mode and exposing said fluid inlet and fluid outlet of said at least one infusion pump unit for allowing access thereto, and a mains supply unit for receiving electric energy from the mains supply and having terminals connectible to said exterior terminals for supplying said electric energy to said power supply unit of said at least one infusion pump unit, said mains supply unit constituting said external electric supply means.

2. The infusion pump system according to claim 1, said electronic control means comprising a microprocessor control means.

3. The infusion pump system according to claim 1, said electronic control means including display means for displaying the operational mode of the infusion pump unit and keyboard means for addressing said electronic control means.

4. The infusion pump system according to claim 3, said keyboard means allowing said electronic control means to be programmed.

5. The infusion pump system according to claim 1, said electronic control means being programmable through an external program port.

6. The infusion pump system according to claim 1, said electronic control means being pre-programmed.

7. The infusion pump system according to claim 1, at least one of said check valves being controllable between a first active state and a second non-active state.

8. The infusion pump system according to claim 7, said inactive state being established by means of a bypass valve establishing in a bypass mode a bypass of said controllable check valve.

9. The infusion pump system according to the claim 1, said controllable pumping system including a reciprocating plunger pump, the operation frequency of which is controllable from said electronic control means for altering the fluid transfer rate of said controllable pumping system.

10. The infusion pump system according to claim 1, said first capacitive detector circuit comprising a capacitive attenuator including a variable capacitor communicating with said pumping system, said capacitive attenuator being supplied with an alternating input signal for generating an alternating output signal including an amplitude modulated component which is detected by an amplitude demodulator circuit.

11. The infusion pump system according to claim 1, further comprising a second capacitive detector circuit for monitoring the operational mode of the pumping system.

12. The infusion pump system according to claim 11, said second capacitive detector circuit comprising a capacitive attenuator including a variable capacitor communicating with said pumping system, said capacitive attenuator being supplied with an alternating input signal for generating an alternating output signal including an amplitude modulated component which is detected by an amplitude demodulator circuit.

13. The infusion pump system according to claim 9, said reciprocating plunger pump including a solenoid actuator and a mechanical attenuator for providing mechanical attenuation of solenoid activated plunger of the plunger pump.

14. An infusion pump unit comprising:

a housing of a size allowing said infusion pump unit to be carried by a user as a portable infusion pump unit, said housing defining an exterior surface, a fluid inlet provided accessibly at said exterior surface for establishing fluid communication from an external infusion bag to said fluid inlet, a fluid outlet provided accessibly at said exterior surface for establish-ing fluid communication to an infusion site, a controllable pumping system included within said housing and having an inlet and an outlet, said inlet being connected to said fluid inlet and said outlet being connected to said fluid outlet for allowing transfer of fluid from said fluid inlet to said fluid outlet through activating said controllable pumping system, a first check valve provided at said inlet of said controllable pumping system, a second check valve provided at said outlet of said controllable pumping system, an electronic control means received within said housing for controlling the operation of said controllable pumping system, said electronic control means including at least two preset pumping programs for allowing said controllable pumping system to be controlled in at least two alternative infusion pumping operations, a power supply unit housed within said housing for supplying power to said controllable pumping system and to said electronic control means and connectible through exterior terminals provided at said exterior surface of said housing to external electric energy supply means, and a first capacitive detector circuit for detecting the presence of infusion liquid or alternatively air within the pumping system;

and to be used in connection with a stationary receptor system including:

a receptor means for receiving and fixating said at least one infusion pump unit therein so as to maintain said at least one infusion pump unit in a stationary mode and exposing said fluid inlet and fluid outlet of said at least one infusion pump unit for allowing access thereto, and a mains supply unit for receiving electric energy from the mains supply and having terminals connectible to said exterior terminals for supplying said electric energy to said power supply unit of said at least one infusion pump unit, said mains supply unit constituting said external electric supply means.

15. The infusion pump system according to claim 14, said electronic control means comprising a microprocessor control means.

16. The infusion pump system according to claim 14, said electronic control means including display means for displaying the operational mode of the infusion pump unit and keyboard means for addressing said electronic control means.

17. The infusion pump system according to claim 16, said keyboard means allowing said electronic control means to be programmed.

18. The infusion pump system according to claim 14, said electronic control means being programmable through an external program port.

19. The infusion pump system according to claim 14, said electronic control means being pre-programmed.

20. The infusion pump system according to claim 14, at least one of said check valves being controllable between a first active state and a second non-active state.

21. The infusion pump system according to claim 14, said inactive state being established by means of a bypass valve establishing in a bypass mode a bypass of said controllable check valve.

22. The infusion pump system according to claim 14, said controllable pumping system including a reciprocating plunger pump, the operation frequency of which is controllable from said electronic control means for altering the fluid transfer rate of said controllable pumping system.

23. The infusion pump system according to claim 14, said first capacitive detector circuit comprising a capacitive attenuator including a variable capacitor communicating with said pumping system, said capacitive attenuator being supplied with an alternating input signal for generating an alternating output signal including an amplitude modulated component which is detected by an amplitude demodulator circuit.

24. The infusion pump system according to claim 14, further comprising a second capacitive detector circuit for monitoring the operational mode of the pumping system.

25. The infusion pump system according to claim 24, said second capacitive detector circuit comprising a capacitive attenuator including a variable capacitor communicating with said pumping system, said capacitive attenuator being supplied with an alternating input signal for generating an alternating output signal including an amplitude modulated component which is detected by an amplitude demodulator circuit.

26. The infusion pump system according to claim 22, said reciprocating plunger pump including a solenoid actuator and a mechanical attenuator for providing mechanical attenuation of solenoid activated plunger of the plunger pump.

* * * * *